(12) United States Patent
Kaplan et al.

(10) Patent No.: US 6,329,566 B1
(45) Date of Patent: Dec. 11, 2001

(54) METHODS FOR THE DETECTION, TREATMENT, AND PREVENTION OF NEURODEGENERATION

(75) Inventors: Joshua M. Kaplan, Berkeley, CA (US); Allison J. Oppenheimer, Cambridge; Anne C. Hart, Boston, both of MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 08/864,785

(22) Filed: May 29, 1997

(51) Int. Cl.[7] .................................................... G01N 33/00
(52) U.S. Cl. ............................................ 800/3; 435/320.1
(58) Field of Search ................................. 424/9.1; 435/6, 435/172.3, 320.1, 325; 800/2, 3

(56) References Cited

PUBLICATIONS

Mendel et al., *Science*, vol. 267, pp. 1652–1655, 1995.*
Foster et al., *American J. Physiology*, vol. 261, pp. 15–20, 1991, Abstract only.*
Svensson et al., "Heterologous expression of the cloned guinea pig α2B, and α2A, α2C adrenoceptor subtypes." *Biochem. Pharmacol.* 51:291–300 (1996).
Waldmann et al., "Functional degenerin–containing chimeras identify residues essential for amiloride–sensitive Na$^+$ channel function." *J. Biol. Chem.* 270:11735–11737 (1995).
Kish et al., "Brain Neurotransmitters in Glycine Encephalopathy", Ann. Neurol. 24(3):458–461, (1988).
Blennow et al., "Influence of Reduced Ocygen Availability on Cerebral Metabolic Changes during Bicuculline–induced Seizures in Rats" J. Cereb. Blood Flow Metab. 5(3):439–445, (1985).
Bernard et al., "Expression of Glutamate Receptors in th Human and Rat Basal Ganglia: Effect of the Dopaminergic Denervation on AMPA Receptor Gene Expression in the Striatopallidal Complex in Parkinson's Disease and Rat with 6–OHDA Lesion", J. Comp. Neurol. 368(4):553–568, (1996).
Hart et al., "Synaptic code for sensory modalities revealed by C. elegans GLR–1 Glutamate receptor", Letters to Nature 378(2):82–85, (1995).
Choi, "Ischemia–induced neuronal apoptosis", Current Opinion in Neurobiology 6:667–672, (1998).
Maricq et al., "Mechanosensory signalling in C. elegans mediated by the GLR–1 glutamate receptor", Nature 378:78–81, (1995).
Hollmann et al., "Cloned Glutamate Receptors", Ann. Rev. Neurosci. 17:31–108, (1994).
Li et al., "Identification of chemical synapses in the pharynx of *Caenorhabditis elegans*", Proc. Nat'l Acad. Sci. (USA) 94:5912–5916, (1997).

Raizen et al., "Electrical activity and behavior in the pharynx of *Caenorhabditis elegans*", Neuron 12:483–495, (1994).
Avery, "The Genetics of feeding in *Caenorhabditis elegans*", Genetics 133:897–917, (1993).
Buisson et al., "The inhibitory mGluR agonist, s–4–carbosy–3–hydroxy–phenylglycine selectively attenuates NMDA neurotoxicity and oxygen–glucose deprivation –induced neuronal death", Neuropharmacology 34:1081–1087, (1995).
Greengard et al., Enhancement of the glutamate response by cAMP–dependent protein kinase in the hippocampal neurons, Science 253:1135–1138, (1991).
Cerne et al., "Enhancement of the N–methyl–D–aspartate response in spinal dorsal horn neurons by cAMP–dependent protein kinase", Neurosci. Letters 161:124–128, (1993).
Raman et al., "β–adrenergic regulation of synaptic NMDA receptors by cAMP–dependent protein kinase", Neuron 16:415–421, (1996).
Colwell et al., "Excitatory synaptic transmission in neostriatal neurons: regulation by cyclic AMP–dependent mechanisms", J. Neurosci. 15:1704–1713, (1995).
Nurrish et al., "The Role of G–Proteins in Serotonin Signaling and Neurotoxicity: An Update from the Kaplan Lab," Abstract, Early 1997 *International Worm Meeting*.
Kass et al., "Isolation and Characterization of GLR–1 Suppressors," Abstract, Early 1997 *International Worm Meeting*.
Rongo et al., "Neurotransmitter Receptor Localization in C. Elegans," Abstract, Early 1997 *International Worm Meeting*.
Hart et al., "Sensory Stimulus Detection and Transduction in a Polymodal Neuron," Abstract, Early 1997 *International Worm Meeting*.
Berger et al., Gα$_s$–Induced Neurodegeneration in *Caenorhabditis elegans*, *The Journal of Neuroscience* 18:2871–2880 (1998).
Korswagen et al, "An Activating Mutation in a *Caenorhabditis elegans* G$_s$ Protein Induces Neural Degeneration," *Genes & Development* 11:1493–1503 (1997).

* cited by examiner

*Primary Examiner*—Gary L. Kunz
*Assistant Examiner*—Stephen Gucker
(74) *Attorney, Agent, or Firm*—Clark & Elbing LLP

(57) ABSTRACT

In general, the invention provides methods for identifying genes involved in neurodegeneration and therapeutics for treating animals with a neurodegenerative disease. Methods and kits for the detection of compounds which enhance neuroprotection and diagnostic kits for the detection of neurodegenerative diseases are also a part of the invention.

16 Claims, 11 Drawing Sheets

Role of cAMP and neural activity in $G_S$-induced neurotoxicity.

Swelling and cytotoxicity caused by the $\alpha_s(gf)$ transgene were quantitated in various genetic backgrounds, as described (9). For each data point 30-80 animals were analyzed.

| mut; $\alpha_s(gf)$ genotype (MUT gene product) | % PVC Swelling | % PVC Degeneration |
|---|---|---|
| + | 88 | 89 |
| Adenylyl cyclase: | | |
| acy-1 (nu327) | 19* | 4* |
| acy-1 (nu327)/+ | 63* | ND |
| acy-1 (nu329) | 0* | 0* |
| acy-1 (nu329)/+ | 27* | ND |
| acy-1 (nu343) | 4* | 0* |
| acy-1 (nu343)/+ | 24* | ND |
| Degeneration: | | |
| deg-1(u506u550) (ENaC) | 83 | 97 |
| mec-6(e1342) | 84 | 91 |
| unc-8(n491n1192) (ENaC) | 91 | 90 |
| Calcium Channels: | | |
| egl-19(n582) (a2 subunit) | 90 | 92 |
| unc-2(e55) ($\alpha 1$ subunit) | 86 | 82 |
| unc-36(e251) ($\alpha 1$ subunit) | 79 | 68* |
| Glutamate signaling: | | |
| glr-1(n2461) (GluR A) | 82 | 95 |
| eat-4(ky5) | 78 | 58* |
| Apoptosis: | | |
| ced-3(n717) (ICE) | 94 | 85 |
| Exocytosis: | | |
| unc-18(e81) (n-Sec1) | 68*¹ | 92‡ |

*Indicates significantly (p<0.005) differs from $\alpha_s$ (gf) single mutants. ¹In addition to the swollen cells, 13% of PVC neurons in unc-18 L1 larvae have condensed morphology characteristic of programmed cell deaths. ‡25% of PVC corpses in unc-18 adults appear to be engulfed by surrounding hypodermal cells.

Fig. 2

MSSWNEAWDRGKQMVGEPLAKMTAAAASATGAAPPQQMQEEGNENPMQMH

SNKVLQVMEQTWIGKCRKRWLLAILANMGFMISFGIRCNFGAAKTHMYKN

YTDPYGKVHMHEFNWTIDELSVMESSYFYGYLVTQIPAGFLAAKFPPNKL

FGFGIGVGAFLNILLPYGFKVKSDYLVAFIQITQGLVQGVCYPAMHGVWR

YWAPPMERSKLATTAFTGSYAGAVLGLPLSAFLVSYVSWAAPFYLYGVCG

VIWAILWFCVTFEKPAFHPTISQEEKIFIEDAIGHVSNTHPTIRSIPWKA

IVTSKPVWAIIVANFARSWTFYLLLQNQLTYMKEALGMKIADSGLLAAIP

HLVMGCVVLMGGQLADYLRSNKILSTTAVRKIFNCGGFGGEAAFMLIVAY

TTSDTTAIMALIAAVGMSGFAISGFNVNHLDIAPRYAAILMGFSNGIGTL

AGLTCPFVTEAFTAHSKHGWTSVFLLASLIHFTGVTFYAVYASGELQEWA

EPKEEEEWSNKELVNKTGINGTGYGAAETTFTQLPAGVDSSYQAQAAPAP

GTNPFASAWDEHGSSGVVENPHYQQW

Fig. 3

Fig. 6 (page 1 of 2)

```
1   ..............................................MDDDVGERTPALGGSCGPSVRAHSSS.PRRV..............PLFERASARWNPQFRSATL   50
                                                  :::..::..:.|:::..:|:::.|||||              ||||:||:|..|.|
1   MASSPHQQLLHHHSTEVSCDSSGDSNSVRVKINPKQLSSNTHPKHCKYSISSSCSSSGDSGGLPRRVGGGRLRRQKKLPQLFERASSRWWDPKFDSMNL  100

51  EAQYWKCSFSQLRDRFRSGLIYIAVVIAAWTLYLAL.FDRTFTQHWIVSLCLCAIIFAMFAFTACAAQYQRFYMPTSFLCTFLICLVTLL.........  139
    |...|.|.|.|:|:.||||:.:.|..:.|.:....|.:|..:.|:..:|:.|.|||..|||||.|.:.|||||||||||||||||||||
101 EEACLERCFPQTQRRFRYALFYVGFACLLWSIYFAVHMKSKVIVMVVPALCFLVVCVGFFLFT.FTKLYARHYAWTSLALTLLVFALTLAAQFQVWTPLS  199
                                    V nu327
140 ........IFSAENQAAFMTPVASLATSFQVVLLIYTVIPLPYLCILIGIIYSILFEILN...KNKIGLEEAG..........YIKLVLHAGVHLLGVHLF  220
            .:.:...::.|:|||||:|::|.||||||||||||||||||||||||||||:|:||     ::|:|||||          ||:||||||||||:||
200 GRVDSSNHTLTATPADTCLSQVGSFSICIEVLLLLYTMQLPLYLSLFLGVVYSVLFETFGYHFRNEDCYPSPGPGALHWELLSRALLHVCIHAIGIHLF  299

221 ILTQVRQRKTFLKVGQSMLARKDLELETQFKDHMIQSVMPKKVADELLKDASE.....LRRPSASNDSNCRTSNATQVDQPLAKMVPEYRKFRPFTMNLM  315
    ::::.|::|:|||||||:..:||:|:|||.:::.||  :::.:.:.:..  ::|                      ::..::|
300 VMSQVRSRSTFLKVGQSIMHGKDLEVEKALKERMIHSVMPRIIADDLMKQGDEESENSVKRHATSSPKNRKKKSSIQ.KAPIA......FRPFKMQQI  390
                                           SD nu329

316 TNVSILFADIAGFTKMSSNKSADELVNLLNDLFGRFDTLCRLRGLEKISTLGDCYYCVAGCPEPCDDHACRTVEMGLDMIVAIRQFDIDRGQEVNMRVGI  415
    :.||||||.||:|||||.:|:.|::||::||:|||||.|.:||||||||||||||||||||:..:|||:::.::||||||||||||:|||||||||
391 EEVSILFADIVGFTKMSANKSAHALVGLLNDLFGRFDRLICEQTKCEKISTLGDCYYCVAGCPEPRADHAYCCIEMGLGMIKAIEQFCQEKKEMVNMRVGV  490

416 HTGKVMCGMVGTKRFKFDVFSNDVTLANEMESSGVAGRVHVSEATAKLLKGLYETEEGPDYDGFLRMQVQGTERRVKPESMKTFFIKGRINDGVEEEVMQ  515
    |||:|:||:|||:||||||||||||:|:||:|.|.||||:|||||||.||:|:.:::                ::|::|:|::|
491 HTGTVICGILGMRRFKFDVWSNDVNLANLMEQLGVAGKVHISEATAKYLDDRYEMEDGRVIE...RLGQSVADQLK..GLKTYLISGQ...........  574

516 VQEVESLHSQKSSKKSTLKQKWAEKLKMNHTNSYPMRAAAREGGGSLRIKLAERNRSTQLLPKESNSICIMEDNRKSASLQALATNNFNGSNTDTNNTYS  615
    ..:.:.......||:..|:...::::                 :::...::.|::..:.:::
575 .RAKESHCSCAEALLSGF......EVIDDSRESSGPRGQGTASPGSVS.DLAQTVKTFDNL.KTCPSCGITFAPKSEAGAEGGTVQNGCQDEPKT.....  660

616 ERGVAGSVSKKKSVAGSESNSIKGSRSSGLQLSLQDGNSDLNSV...GGLDTAISHHHNAASLTRF.DTDNNFDQRLAMVIGQEGGFDKGFWNHHDSLMK  711
    ::|:                                        :|::|::                          |::..|:..::.:.|
661 ........STKASGGPNSKTQNGLLSPPAEEKLTNSQTSLCEILQEKGRWAGVSLDQSALLPLRFKNIREKTDAHFVDI..KEDSLMKDYF.FKPPINQ  749
```

Fig. 6 (page 1 of 2)

```
712  WTLRFNEKDVEEEYRAHFVDSSERYTASKKGHVERHKDLMEQGGEKDGITGSTVNKY...RYSGVFIDIIVATLIFVIS......GAVAIMSVRPFPLS  801
     :.|.:::.||.:                                           :::...:|.:  :: ::.|:::::  —|—|.|
750  FSLNFLDQELERSYRTSY.........................................QEEVIKNSPVKTFASATFSSLLDVFLSTTVFLILSITCFLKYGATATPPPAALAV  823

802  LIAYFPFAAAILLITTVLIGL...PLLARKKSFQCANQWMPRHLIGLLLIFLPIGVAICIMPLCQSGDCANVILNYRLAFSYVTILAIFAHCNFSQLAAW  898
     : :.|:::.|  |||:::.    :| ||||||  :: ..|:::   :: :. :|:.   |:.:  .| ::  .|:  || ::::.:|||||.:|  |
824  FGADLLEVLSLIVSIRMVFFLEDVMTCTKWLLEWIAGWLPRHCIGAILVSLP.ALAVYSHITSEFETNIHVTM...FTGSAV.LVAVVHYCNFCQLSSW  918
                           SD nu343
                              →
899  PKTTAAVFIGLLHIAGVFYCEFNLKHLVEEQDTCNVTAIMIPPIRKGLNYTIALNSTSARTLSQD.FGSPLFIWELLLDVILSIVLVAFLNYQFETAFRM  997
     : ..|:.|.  :   :|||   ..:  :  :||   :.:  ::|.||: ::.||  :||||||  ::..|  .||:|:|||:::.|||||||||:|:
919  MRSSLATIVG..AGLL......LLLHISLCQDSSIVMSPLDSAQNFSAQRNPCNSSVLQDGRRPASLIGKELILTFFLLLLVWFLNREFEVSYRL  1006

998  SFFGDVQARRDTERMQIVRDQADWLLNNVIPAHAVESLKTDTKYSENHETVGVLFASITNWNDMYEENFEGGREFLRVLNEVIGDFDELLDRPDFTHIEK  1097
     : |  .||||||||||:|:||||||||:|  :: ..|:  |:|||: :|:.| |:| |.:|||.||||||:  :  ||||||||:|||:|::::|||
1007 HYHGDVEADLHRTKIQSMRDQADWLLRNIIPYHVAEQLKVSQTYSKNHEDSGGVIFASIVNFSEFYEENYEGGKECYRVLNELIGDFDELLSKPDYNSIEK  1106

1098 IKTIGPAYMAASGLNPERKKNMLHPKEHLYQMVDFALAVQHVLSVFNEDLLNFDFVCKLGLNIGPVTAGVIGTTKLYYDIWGDTVNIASRMYSTGVLNRI  1197
     ||||||:|||||||||||:||::|.;  ||||||.|.||||||||||||||||||||||||||||||||||||:||||||||||||:|:|||||||||
1107 IKTIGATYMAASGLNTAQCQEGGHPQEHLRILFEFAKEMMRVVDDFNNNMLWFNFKLRVGFNHGPLTAGVIGTTKLLYDIWGDTVNIASRMDTTGVECRI  1206

1198 QVSQHTREYLLDR.YEFEFRDHIEVKGIDGGMDTYLLVGRKGDIPP.....................SIKDNQEDEF*.........................  1254
     ||||..|:||:|:.  .:. |:|||:|||::|||||||| |||||                     .|:::|
1207 QVSEESYRVLSKMGYDFDYRGTVNVKG.KGQMKTYLYPKCTDNGVVPQHQLSISPDIRVQVDGSIGRSPTDEIANLVPSVQYSDKASLGSDDSTQAKEAR  1305
```

Fig. 6 (page 2 of 2)

SEQUENCE LISTING

<160> NUMBER OF SEQ ID NOS: 3

<210> SEQ ID NO 1
<211> LENGTH: 576
<212> TYPE: PRT
<213> ORGANISM: Caenorhabditis elegans

<400> SEQUENCE: 1

```
Met Ser Ser Trp Asn Glu Ala Trp Asp Arg Gly Lys Gln Met Val Gly
 1               5                  10                  15

Glu Pro Leu Ala Lys Met Thr Ala Ala Ala Ser Ala Thr Gly Ala
                20                  25                  30

Ala Pro Pro Gln Gln Met Gln Glu Glu Gly Asn Glu Asn Pro Met Gln
                35                  40                  45

Met His Ser Asn Lys Val Leu Gln Val Met Glu Gln Thr Trp Ile Gly
        50                  55                  60

Lys Cys Arg Lys Arg Trp Leu Leu Ala Ile Leu Ala Asn Met Gly Phe
65                  70                  75                  80

Met Ile Ser Phe Gly Ile Arg Cys Asn Phe Gly Ala Ala Lys Thr His
                85                  90                  95

Met Tyr Lys Asn Tyr Thr Asp Pro Tyr Gly Lys Val His Met His Glu
                100                 105                 110

Phe Asn Trp Thr Ile Asp Glu Leu Ser Val Met Glu Ser Ser Tyr Phe
            115                 120                 125

Tyr Gly Tyr Leu Val Thr Gln Ile Pro Ala Gly Phe Leu Ala Ala Lys
    130                 135                 140

Phe Pro Pro Asn Lys Leu Phe Gly Phe Gly Ile Gly Val Gly Ala Phe
145                 150                 155                 160

Leu Asn Ile Leu Leu Pro Tyr Gly Phe Lys Val Lys Ser Asp Tyr Leu
                165                 170                 175

Val Ala Phe Ile Gln Ile Thr Gln Gly Leu Val Gln Gly Val Cys Tyr
                180                 185                 190

Pro Ala Met His Gly Val Trp Arg Tyr Trp Ala Pro Pro Met Glu Arg
                195                 200                 205

Ser Lys Leu Ala Thr Thr Ala Phe Thr Gly Ser Tyr Ala Gly Ala Val
        210                 215                 220

Leu Gly Leu Pro Leu Ser Ala Phe Leu Val Ser Tyr Val Ser Trp Ala
225                 230                 235                 240

Ala Pro Phe Tyr Leu Tyr Gly Val Cys Gly Val Ile Trp Ala Ile Leu
                245                 250                 255

Trp Phe Cys Val Thr Phe Glu Lys Pro Ala Phe His Pro Thr Ile Ser
                260                 265                 270

Gln Glu Glu Lys Ile Phe Ile Glu Asp Ala Ile Gly His Val Ser Asn
            275                 280                 285

Thr His Pro Thr Ile Arg Ser Ile Pro Trp Lys Ala Ile Val Thr Ser
    290                 295                 300

Lys Pro Val Trp Ala Ile Ile Val Ala Asn Phe Ala Arg Ser Trp Thr
305                 310                 315                 320

Phe Tyr Leu Leu Leu Gln Asn Gln Leu Thr Tyr Met Lys Glu Ala Leu
                325                 330                 335

Gly Met Lys Ile Ala Asp Ser Gly Leu Leu Ala Ala Ile Pro His Leu
                340                 345                 350

Val Met Gly Cys Val Val Leu Met Gly Gly Gln Leu Ala Asp Tyr Leu
```

-continued

```
                355                 360                 365
Arg Ser Asn Lys Ile Leu Ser Thr Thr Ala Val Arg Lys Ile Phe Asn
    370                 375                 380
Cys Gly Gly Phe Gly Gly Glu Ala Ala Phe Met Leu Ile Val Ala Tyr
385                 390                 395                 400
Thr Thr Ser Asp Thr Thr Ala Ile Met Ala Leu Ile Ala Ala Val Gly
                405                 410                 415
Met Ser Gly Phe Ala Ile Ser Gly Phe Asn Val Asn His Leu Asp Ile
                420                 425                 430
Ala Pro Arg Tyr Ala Ala Ile Leu Met Gly Phe Ser Asn Gly Ile Gly
            435                 440                 445
Thr Leu Ala Gly Leu Thr Cys Pro Phe Val Thr Glu Ala Phe Thr Ala
    450                 455                 460
His Ser Lys His Gly Trp Thr Ser Val Phe Leu Leu Ala Ser Leu Ile
465                 470                 475                 480
His Phe Thr Gly Val Thr Phe Tyr Ala Val Tyr Ala Ser Gly Glu Leu
                485                 490                 495
Gln Glu Trp Ala Glu Pro Lys Glu Glu Glu Trp Ser Asn Lys Glu
                500                 505                 510
Leu Val Asn Lys Thr Gly Ile Asn Gly Thr Tyr Gly Ala Ala Glu
            515                 520                 525
Thr Thr Phe Thr Gln Leu Pro Ala Gly Val Asp Ser Ser Tyr Gln Ala
    530                 535                 540
Gln Ala Ala Pro Ala Pro Gly Thr Asn Pro Phe Ala Ser Ala Trp Asp
545                 550                 555                 560
Glu His Gly Ser Ser Gly Val Val Glu Asn Pro His Tyr Gln Gln Trp
                565                 570                 575

<210> SEQ ID NO 2
<211> LENGTH: 1253
<212> TYPE: PRT
<213> ORGANISM: Caenorhabditis elegans

<400> SEQUENCE: 2

Met Asp Asp Asp Val Gly Glu Arg Thr Pro Ala Leu Gly Gly Ser Cys
1               5                   10                  15
Gly Pro Ser Val Arg Ala His Ser Ser Pro Arg Arg Val Pro Leu
            20                  25                  30
Phe Glu Arg Ala Ser Ala Arg Trp Trp Asn Pro Gln Phe Arg Ser Ala
        35                  40                  45
Thr Leu Glu Ala Gln Tyr Trp Lys Cys Ser Phe Ser Gln Leu Arg Asp
    50                  55                  60
Arg Phe Arg Ser Gly Leu Ile Tyr Ile Ala Val Val Ile Ala Ala Trp
65                  70                  75                  80
Thr Leu Tyr Leu Ala Leu Phe Asp Arg Thr Phe Ile Gln His Trp Ile
                85                  90                  95
Val Ser Leu Cys Leu Cys Ala Ile Ile Phe Ala Met Phe Ala Phe Thr
                100                 105                 110
Ala Cys Ala Ala Gln Tyr Gln Arg Phe Tyr Met Pro Thr Ser Phe Leu
            115                 120                 125
Cys Thr Phe Leu Ile Cys Leu Val Thr Leu Leu Ile Phe Ser Ala Glu
    130                 135                 140
Asn Gln Ala Ala Phe Met Thr Pro Val Ala Ser Leu Ala Thr Ser Phe
145                 150                 155                 160
```

```
Gln Val Val Leu Leu Ile Tyr Thr Val Ile Pro Leu Pro Leu Tyr Leu
            165                 170                 175
Cys Ile Leu Ile Gly Ile Ile Tyr Ser Ile Leu Phe Glu Ile Leu Asn
            180                 185                 190
Lys Asn Lys Ile Gly Leu Glu Glu Ala Gly Tyr Ile Lys Leu Val Leu
            195                 200                 205
His Ala Gly Val His Leu Leu Gly Val His Leu Phe Ile Leu Thr Gln
        210                 215                 220
Val Arg Gln Arg Lys Thr Phe Leu Lys Val Gly Gln Ser Met Leu Ala
225                 230                 235                 240
Arg Lys Asp Leu Glu Leu Glu Thr Gln Phe Lys Asp His Met Ile Gln
                245                 250                 255
Ser Val Met Pro Lys Lys Val Ala Asp Glu Leu Leu Lys Asp Ala Ser
            260                 265                 270
Glu Leu Arg Arg Pro Ser Ala Ser Asn Asp Ser Asn Cys Arg Thr Ser
            275                 280                 285
Asn Ala Thr Gln Val Asp Gln Pro Leu Ala Lys Met Val Pro Glu Tyr
        290                 295                 300
Arg Lys Phe Arg Pro Phe Thr Met Asn Leu Met Thr Asn Val Ser Ile
305                 310                 315                 320
Leu Phe Ala Asp Ile Ala Gly Phe Thr Lys Met Ser Ser Asn Lys Ser
                325                 330                 335
Ala Asp Glu Leu Val Asn Leu Leu Asn Asp Leu Phe Gly Arg Phe Asp
            340                 345                 350
Thr Leu Cys Arg Leu Arg Gly Leu Glu Lys Ile Ser Thr Leu Gly Asp
            355                 360                 365
Cys Tyr Tyr Cys Val Ala Gly Cys Pro Glu Pro Cys Asp Asp His Ala
        370                 375                 380
Cys Arg Thr Val Glu Met Gly Leu Asp Met Ile Val Ala Ile Arg Gln
385                 390                 395                 400
Phe Asp Ile Asp Arg Gly Gln Glu Val Asn Met Arg Val Gly Ile His
                405                 410                 415
Thr Gly Lys Val Met Cys Gly Met Val Gly Thr Lys Arg Phe Lys Phe
            420                 425                 430
Asp Val Phe Ser Asn Asp Val Thr Leu Ala Asn Glu Met Glu Ser Ser
            435                 440                 445
Gly Val Ala Gly Arg Val His Val Ser Glu Ala Thr Ala Lys Leu Leu
        450                 455                 460
Lys Gly Leu Tyr Glu Ile Glu Glu Gly Pro Asp Tyr Asp Gly Pro Leu
465                 470                 475                 480
Arg Met Gln Val Gln Gly Thr Glu Arg Arg Val Lys Pro Glu Ser Met
                485                 490                 495
Lys Thr Phe Phe Ile Lys Gly Arg Ile Asn Asp Gly Val Glu Glu Glu
            500                 505                 510
Val Met Gln Val Gln Glu Val Glu Ser Leu His Ser Gln Lys Ser Ser
            515                 520                 525
Lys Lys Ser Thr Leu Lys Gln Lys Trp Ala Glu Lys Leu Lys Met Asn
        530                 535                 540
His Thr Asn Ser Tyr Pro Met Arg Ala Ala Ala Arg Glu Gly Gly Gly
545                 550                 555                 560
Ser Leu Arg Ile Lys Leu Ala Glu Arg Asn Arg Ser Thr Gln Leu Leu
                565                 570                 575
Pro Lys Glu Ser Asn Ser Ile Cys Ile Met Glu Asp Asn Arg Lys Ser
```

-continued

```
                  580                 585                 590
Ala Ser Leu Gln Ala Leu Ala Thr Asn Asn Phe Asn Gly Ser Asn Thr
            595                 600                 605

Asp Thr Asn Asn Thr Tyr Ser Glu Arg Gly Val Ala Gly Ser Val Ser
            610                 615                 620

Lys Lys Ser Val Ala Gly Ser Glu Ser Asn Ser Ile Lys Gly Ser Arg
625                 630                 635                 640

Ser Ser Gly Leu Gln Leu Ser Leu Gln Asp Gly Asn Ser Asp Leu Asn
                645                 650                 655

Ser Val Gly Gly Leu Asp Thr Ala Ile Ser His His Asn Ala Ala
            660                 665                 670

Ser Leu Thr Arg Phe Asp Thr Asp Asn Asn Phe Asp Gln Arg Leu Ala
            675                 680                 685

Met Val Ile Gly Gln Gly Glu Gly Gly Phe Asp Lys Gly Phe Trp Asn
            690                 695                 700

His His Asp Ser Leu Asn Lys Trp Thr Leu Arg Phe Asn Glu Lys Asp
705                 710                 715                 720

Val Glu Glu Glu Tyr Arg Ala His Phe Val Asp Ser Ser Glu Arg Tyr
                725                 730                 735

Thr Ala Ser Lys Lys Gly His Val Glu Arg His Lys Asp Leu Met Glu
            740                 745                 750

Gln Gly Gly Glu Lys Asp Gly Ile Thr Gly Ser Thr Val Asn Lys Tyr
            755                 760                 765

Arg Tyr Ser Gly Val Phe Ile Asp Ile Ile Val Ala Thr Leu Ile Phe
            770                 775                 780

Val Ile Ser Gly Ala Val Ala Ile Met Ser Val Arg Pro Phe Pro Leu
785                 790                 795                 800

Ser Leu Ile Ala Tyr Phe Pro Phe Ala Ala Ile Leu Ile Leu Thr
                805                 810                 815

Ile Val Leu Ile Gly Leu Pro Leu Leu Ala Arg Lys Lys Ser Phe Gln
                820                 825                 830

Cys Ala Asn Gln Trp Met Pro Arg His Leu Ile Gly Leu Leu Leu Ile
            835                 840                 845

Phe Leu Pro Ile Gly Val Ala Ile Cys Ile Met Pro Leu Cys Gln Ser
850                 855                 860

Gly Asp Cys Ala Asn Val Ile Leu Asn Tyr Arg Leu Ala Phe Ser Tyr
865                 870                 875                 880

Val Thr Ile Leu Ala Ile Phe Ala His Cys Asn Phe Ser Gln Leu Ala
                885                 890                 895

Ala Trp Pro Lys Thr Thr Ala Ala Val Phe Ile Gly Leu Leu His Ile
            900                 905                 910

Ala Gly Val Phe Tyr Cys Glu Phe Asn Leu Lys His Leu Val Glu Glu
            915                 920                 925

Gln Asp Thr Cys Asn Val Thr Ala Ile Met Ile Pro Pro Ile Arg Lys
930                 935                 940

Gly Leu Asn Tyr Thr Ile Ala Leu Asn Ser Thr Ser Ala Arg Thr Leu
945                 950                 955                 960

Ser Gln Asp Phe Gly Ser Pro Leu Phe Ile Trp Glu Leu Leu Leu Asp
                965                 970                 975

Val Ile Leu Ser Ile Val Leu Val Ala Phe Leu Asn Tyr Gln Phe Glu
                980                 985                 990

Thr Ala Phe Arg Met Ser Phe Phe Gly Asp Val Gln Ala Arg Arg Asp
            995                 1000                1005
```

```
Thr Glu Arg Met Gln Ile Val Arg Asp Gln Ala Asp Trp Leu Leu Asn
    1010                1015                1020

Asn Val Ile Pro Ala His Ala Val Glu Ser Leu Lys Thr Asp Thr Lys
1025                1030                1035                104

Tyr Ser Glu Asn His Glu Thr Val Gly Val Leu Phe Ala Ser Ile Thr
                1045                1050                1055

Asn Trp Asn Asp Met Tyr Glu Glu Asn Phe Glu Gly Gly Arg Glu Phe
            1060                1065                1070

Leu Arg Val Leu Asn Glu Val Ile Gly Asp Phe Asp Glu Leu Leu Asp
        1075                1080                1085

Arg Pro Asp Phe Thr His Ile Glu Lys Ile Lys Thr Ile Gly Pro Ala
    1090                1095                1100

Tyr Met Ala Ala Ser Gly Leu Asn Pro Glu Arg Lys Lys Asn Met Leu
1105                1110                1115                112

His Pro Lys Glu His Leu Tyr Gln Met Val Asp Phe Ala Leu Ala Val
                1125                1130                1135

Gln His Val Leu Ser Val Phe Asn Glu Asp Leu Leu Asn Phe Asp Phe
            1140                1145                1150

Val Cys Lys Leu Gly Leu Asn Ile Gly Pro Val Thr Ala Gly Val Ile
        1155                1160                1165

Gly Thr Thr Lys Leu Tyr Tyr Asp Ile Trp Gly Asp Thr Val Asn Ile
    1170                1175                1180

Ala Ser Arg Met Tyr Ser Thr Gly Val Leu Asn Arg Ile Gln Val Ser
1185                1190                1195                120

Gln His Thr Arg Glu Tyr Leu Leu Asp Arg Tyr Glu Phe Glu Phe Arg
                1205                1210                1215

Asp His Ile Glu Val Lys Gly Ile Asp Gly Gly Met Asp Thr Tyr Leu
            1220                1225                1230

Leu Val Gly Arg Lys Gly Asp Gly Ile Pro Pro Ser Ile Lys Asp Asn
        1235                1240                1245

Gln Glu Asp Glu Phe
    1250

<210> SEQ ID NO 3
<211> LENGTH: 1305
<212> TYPE: PRT
<213> ORGANISM: Mus musculus

<400> SEQUENCE: 3

Met Ala Ser Ser Pro His Gln Gln Leu Leu His His Ser Thr Glu
 1               5                  10                  15

Val Ser Cys Asp Ser Ser Gly Asp Ser Asn Ser Val Arg Val Lys Ile
                20                  25                  30

Asn Pro Lys Gln Leu Ser Ser Asn Thr His Pro Lys His Cys Lys Tyr
            35                  40                  45

Ser Ile Ser Ser Cys Ser Ser Gly Asp Ser Gly Leu Pro
    50                  55                  60

Arg Arg Val Gly Gly Gly Arg Leu Arg Arg Gln Lys Lys Leu Pro
65                  70                  75                  80

Gln Leu Phe Glu Arg Ala Ser Ser Arg Trp Trp Asp Pro Lys Phe Asp
                85                  90                  95

Ser Met Asn Leu Glu Glu Ala Cys Leu Glu Arg Cys Phe Pro Gln Thr
                100                 105                 110

Gln Arg Arg Phe Arg Tyr Ala Leu Phe Tyr Val Gly Phe Ala Cys Leu
```

-continued

```
            115                 120                 125
Leu Trp Ser Ile Tyr Phe Ala Val His Met Lys Ser Lys Val Ile Val
        130                 135                 140

Met Val Val Pro Ala Leu Cys Phe Leu Val Val Cys Val Gly Phe Phe
145                 150                 155                 160

Leu Phe Thr Phe Thr Lys Leu Tyr Ala Arg His Tyr Ala Trp Thr Ser
                165                 170                 175

Leu Ala Leu Thr Leu Leu Val Phe Ala Leu Thr Leu Ala Ala Gln Phe
                180                 185                 190

Gln Val Trp Thr Pro Leu Ser Gly Arg Val Asp Ser Ser Asn His Thr
            195                 200                 205

Leu Thr Ala Thr Pro Ala Asp Thr Cys Leu Ser Gln Val Gly Ser Phe
        210                 215                 220

Ser Ile Cys Ile Glu Val Leu Leu Leu Tyr Thr Val Met Gln Leu
225                 230                 235                 240

Pro Leu Tyr Leu Ser Leu Phe Leu Gly Val Val Tyr Ser Val Leu Phe
                245                 250                 255

Glu Thr Phe Gly Tyr His Phe Arg Asn Glu Asp Cys Tyr Pro Ser Pro
                260                 265                 270

Gly Pro Gly Ala Leu His Trp Glu Leu Leu Ser Arg Ala Leu Leu His
            275                 280                 285

Val Cys Ile His Ala Ile Gly Ile His Leu Phe Val Met Ser Gln Val
        290                 295                 300

Arg Ser Arg Ser Thr Phe Leu Lys Val Gly Gln Ser Ile Met His Gly
305                 310                 315                 320

Lys Asp Leu Glu Val Glu Lys Ala Leu Lys Glu Arg Met Ile His Ser
                325                 330                 335

Val Met Pro Arg Ile Ile Ala Asp Asp Leu Met Lys Gln Gly Asp Glu
                340                 345                 350

Glu Ser Glu Asn Ser Val Lys Arg His Ala Thr Ser Ser Pro Lys Asn
            355                 360                 365

Arg Lys Lys Lys Ser Ser Ile Gln Lys Ala Pro Ile Ala Phe Arg Pro
        370                 375                 380

Phe Lys Met Gln Gln Ile Glu Glu Val Ser Ile Leu Phe Ala Asp Ile
385                 390                 395                 400

Val Gly Phe Thr Lys Met Ser Ala Asn Lys Ser Ala His Ala Leu Val
                405                 410                 415

Gly Leu Leu Asn Asp Leu Phe Gly Arg Phe Asp Arg Leu Cys Glu Gln
            420                 425                 430

Thr Lys Cys Glu Lys Ile Ser Thr Leu Gly Asp Cys Tyr Tyr Cys Val
        435                 440                 445

Ala Gly Cys Pro Glu Pro Arg Ala Asp His Ala Tyr Cys Cys Ile Glu
    450                 455                 460

Met Gly Leu Gly Met Ile Lys Ala Ile Glu Gln Phe Cys Gln Glu Lys
465                 470                 475                 480

Lys Glu Met Val Asn Met Arg Val Gly Val His Thr Gly Thr Val Leu
                485                 490                 495

Cys Gly Ile Leu Gly Met Arg Arg Phe Lys Phe Asp Val Trp Ser Asn
                500                 505                 510

Asp Val Asn Leu Ala Asn Leu Met Glu Gln Leu Gly Val Ala Gly Lys
            515                 520                 525

Val His Ile Ser Glu Ala Thr Ala Lys Tyr Leu Asp Asp Arg Tyr Glu
        530                 535                 540
```

-continued

```
Met Glu Asp Gly Arg Val Ile Glu Arg Leu Gly Gln Ser Val Val Ala
545                 550                 555                 560

Asp Gln Leu Lys Gly Leu Lys Thr Tyr Leu Ile Ser Gly Gln Arg Ala
            565                 570                 575

Lys Glu Ser His Cys Ser Cys Ala Glu Ala Leu Leu Ser Gly Phe Glu
                580                 585                 590

Val Ile Asp Asp Ser Arg Glu Ser Ser Gly Pro Arg Gly Gln Gly Thr
            595                 600                 605

Ala Ser Pro Gly Ser Val Ser Asp Leu Ala Gln Thr Val Lys Thr Phe
610                 615                 620

Asp Asn Leu Lys Thr Cys Pro Ser Cys Gly Ile Thr Phe Ala Pro Lys
625                 630                 635                 640

Ser Glu Ala Gly Ala Glu Gly Thr Val Gln Asn Gly Cys Gln Asp
                645                 650                 655

Glu Pro Lys Thr Ser Thr Lys Ala Ser Gly Gly Pro Asn Ser Lys Thr
                660                 665                 670

Gln Asn Gly Leu Leu Ser Pro Ala Glu Glu Lys Leu Thr Asn Ser
            675                 680                 685

Gln Thr Ser Leu Cys Glu Ile Leu Gln Glu Lys Gly Arg Trp Ala Gly
            690                 695                 700

Val Ser Leu Asp Gln Ser Ala Leu Leu Pro Leu Arg Phe Lys Asn Ile
705                 710                 715                 720

Arg Glu Lys Thr Asp Ala His Phe Val Asp Val Ile Lys Glu Asp Ser
                725                 730                 735

Leu Met Lys Asp Tyr Phe Phe Lys Pro Pro Ile Asn Gln Phe Ser Leu
            740                 745                 750

Asn Phe Leu Asp Gln Glu Leu Glu Arg Ser Tyr Arg Thr Ser Tyr Gln
            755                 760                 765

Glu Glu Val Ile Lys Asn Ser Pro Val Lys Thr Phe Ala Ser Ala Thr
770                 775                 780

Phe Ser Ser Leu Leu Asp Val Phe Leu Ser Thr Thr Val Phe Leu Ile
785                 790                 795                 800

Leu Ser Ile Thr Cys Phe Leu Lys Tyr Gly Ala Thr Ala Thr Pro Pro
                805                 810                 815

Pro Pro Ala Ala Leu Ala Val Phe Gly Ala Asp Leu Leu Glu Val
            820                 825                 830

Leu Ser Leu Ile Val Ser Ile Arg Met Val Phe Phe Leu Glu Asp Val
            835                 840                 845

Met Thr Cys Thr Lys Trp Leu Leu Glu Trp Ile Ala Gly Trp Leu Pro
850                 855                 860

Arg His Cys Ile Gly Ala Ile Leu Val Ser Leu Pro Ala Leu Ala Val
865                 870                 875                 880

Tyr Ser His Ile Thr Ser Glu Phe Glu Thr Asn Ile His Val Thr Met
                885                 890                 895

Phe Thr Gly Ser Ala Val Leu Val Ala Val His Tyr Cys Asn Phe
            900                 905                 910

Cys Gln Leu Ser Ser Trp Met Arg Ser Ser Leu Ala Thr Ile Val Gly
            915                 920                 925

Ala Gly Leu Leu Leu Leu His Ile Ser Leu Cys Gln Asp Ser Ser
            930                 935                 940

Ile Val Met Ser Pro Leu Asp Ser Ala Gln Asn Phe Ser Ala Gln Arg
945                 950                 955                 960
```

```
Asn Pro Cys Asn Ser Ser Val Leu Gln Asp Gly Arg Arg Pro Ala Ser
            965                 970                 975

Leu Ile Gly Lys Glu Leu Ile Leu Thr Phe Phe Leu Leu Leu Leu Leu
            980                 985                 990

Val Trp Phe Leu Asn Arg Glu Phe Glu Val Ser Tyr Arg Leu His Tyr
    995                 1000                1005

His Gly Asp Val Glu Ala Asp Leu His Arg Thr Lys Ile Gln Ser Met
    1010                1015                1020

Arg Asp Gln Ala Asp Trp Leu Leu Arg Asn Ile Ile Pro Tyr His Val
1025                1030                1035                104

Ala Glu Gln Leu Lys Val Ser Gln Thr Tyr Ser Lys Asn His Asp Ser
                1045                1050                1055

Gly Gly Val Ile Phe Ala Ser Ile Val Asn Phe Ser Glu Phe Tyr Glu
                1060                1065                1070

Glu Asn Tyr Glu Gly Gly Lys Glu Cys Tyr Arg Val Leu Asn Glu Leu
            1075                1080                1085

Ile Gly Asp Phe Asp Glu Leu Leu Ser Lys Pro Asp Tyr Asn Ser Ile
            1090                1095                1100

Glu Lys Ile Lys Thr Ile Gly Ala Thr Tyr Met Ala Ala Ser Gly Leu
1105                1110                1115                112

Asn Thr Ala Gln Cys Gln Glu Gly Gly His Pro Gln Glu His Leu Arg
                1125                1130                1135

Ile Leu Phe Glu Phe Ala Lys Glu Met Met Arg Val Val Asp Asp Phe
            1140                1145                1150

Asn Asn Asn Met Leu Trp Phe Asn Phe Lys Leu Arg Val Gly Phe Asn
                1155                1160                1165

His Gly Pro Leu Thr Ala Gly Val Ile Gly Thr Thr Lys Leu Leu Tyr
    1170                1175                1180

Asp Ile Trp Gly Asp Thr Val Asn Ile Ala Ser Arg Met Asp Thr Thr
1185                1190                1195                120

Gly Val Glu Cys Arg Ile Gln Val Ser Glu Glu Ser Tyr Arg Val Leu
                1205                1210                1215

Ser Lys Met Gly Tyr Asp Phe Asp Tyr Arg Gly Thr Val Asn Val Lys
                1220                1225                1230

Gly Lys Gly Gln Met Lys Thr Tyr Leu Tyr Pro Lys Cys Thr Asp Asn
            1235                1240                1245

Gly Val Val Pro Gln His Gln Leu Ser Ile Ser Pro Asp Ile Arg Val
    1250                1255                1260

Gln Val Asp Gly Ser Ile Gly Arg Ser Pro Thr Asp Glu Ile Ala Asn
1265                1270                1275                128

Leu Val Pro Ser Val Gln Tyr Ser Asp Lys Ala Ser Leu Gly Ser Asp
                1285                1290                1295

Asp Ser Thr Gln Ala Lys Glu Ala Arg
            1300                1305
```

METHODS FOR THE DETECTION, TREATMENT, AND PREVENTION OF NEURODEGENERATION

STATEMENT AS TO FEDERALLY SPONSORED RESEARCH

This invention was made in part with support from the Federal government through NIH Grant No. 1RO1NS32196-04. The Federal government has certain rights in the invention.

BACKGROUND OF THE INVENTION

The invention relates to methods and reagents for diagnosing, treating, and preventing neurodegeneration.

Loss of neurons by a degenerative process is a major pathological feature of many human neurological disorders. Neuronal cell death can occur as a result of a variety of conditions including traumatic injury, ischemia, neurodegenerative diseases (e.g., Parkinson's disease, Huntington's disease, Alzheimer's disease, amyotrophic lateral sclerosis (ALS), stroke, or trauma), or as a normal part of tissue development and maintenance. Several inherited disorders produce late onset neuron loss, each of which is highly specific for particular neural cell types. Nine genes have been cloned that are associated with susceptibility to these various neurological disorders (e.g., Huntington's disease, ataxin, and ALS); however, only in the case of Kennedy's syndrome is the biochemical function of the affected gene, the androgen receptor, understood (La Spada et al., Nature 352: 77–79, 1991). Epileptic seizures and stroke also produce neurodegeneration in humans and rodents.

SUMMARY OF THE INVENTION

In general, the invention features methods for the detection, treatment, and prevention of disorders involving neurodegeneration.

In a first aspect, the invention features a method for identifying a compound to treat or prevent the onset of a neurodegenerative disorder. The method involves contacting a cell that includes a reporter gene operably linked to a cAMP regulatory gene or promoter with a candidate compound and measuring the expression of the reporter gene, where a change in reporter gene expression in response to the candidate compound identifies a compound that is useful to treat or prevent the onset of a neurodegenerative disorder.

In various preferred embodiments of the first aspect of the invention, the cAMP regulatory gene may be an acy-1 gene, an eat-4 gene, an unc-36 gene, or a glutamate receptor-encoding gene. In another preferred embodiment, the change in reporter gene expression is a decrease in expression.

In a second aspect, the invention features a cell for identifying a compound to treat or prevent the onset of a neurodegenerative disorder that includes a reporter gene operably linked to a cAMP regulatory gene or promoter.

In various embodiments of the above aspects, the cell is present in an animal, which may be a nematode (e.g., C. elegans) or a mammal (e.g., a rodent).

In a third aspect, the invention features a method for treating or preventing the onset of a neurodegenerative disorder in a mammal that includes administering to the mammal a therapeutically effective amount of a compound that decreases a neuronal cAMP level. In a preferred embodiment of this aspect of the invention, the mammal is a human.

In a fourth aspect, the invention features a method for identifying a mammal (for example, a human) having or likely to develop a neurodegenerative disorder which includes determining whether the mammal has an increased level of cellular cAMP in a neuron, where an increased level indicates that the mammal has or is likely to develop a neurodegenerative disorder.

In a fifth aspect, the invention features a method for identifying a mammal (for example, a human) having or likely to develop a neurodegenerative disorder which involves determining whether the mammal has a mutation in a cAMP regulatory gene. In various preferred embodiments of this aspect, the mutation is in an adenylyl cyclase gene (e.g., the acy-1 gene), or in an unc-36 or eat-4 gene. In other preferred embodiments, the mutation is in a gene encoding a $G\alpha_s$ subunit; and the mutation results in an increase in a neuronal cAMP level.

In a preferred embodiment of various aspects of the invention, the neurodegenerative disorder is Parkinson's disease, Huntington's disease, amyotrophic lateral sclerosis, multiple sclerosis, Alzheimer's disease, stroke, or epilepsy.

In a sixth aspect, the invention features a method for identifying a gene involved in neurodegeneration that involves providing a nematode (for example, C. elegans) that includes an expression construct that includes a promoter derived from a cAMP regulatory gene operably linked to a reporter gene, isolating a mutant of the nematode exhibiting an altered level of reporter gene expression, and identifying the gene comprising the mutation, wherein the gene is involved in neurodegeneration.

In a seventh aspect, the invention features a method for identifying a gene involved in neurodegeneration that involves providing a nematode (for example, C. elegans) that includes a glutamate receptor (GluR) promoter operably linked to a gene encoding a GTP-ase defective $G\alpha_s$ subunit, isolating a mutant of the nematode exhibiting a decreased level of paralysis and neurodegeneration, and identifying the gene that includes the mutation, wherein the gene is involved in neurodegeneration.

In an eighth aspect, the invention features a mammalian (for example, a human) EAT-4 polypeptide, and a vector and cell containing the nucleic acid.

In a final aspect, the invention provides a method for identifying a gene involved in neurodegeneration involving the steps of a) providing a cell that includes a cAMP regulatory gene promoter operably linked to a reporter gene; b) introducing into the cell a candidate gene capable of expressing a candidate protein; and c) measuring reporter gene expression in the cell, where an increase in reporter gene expression in the presence of the candidate protein indicates that the candidate gene is involved in neurodegeneration.

In preferred embodiments, the cell is yeast; and the cAMP regulatory gene is an acy-1 gene, an eat-4 gene, an unc-36 gene, or a glutamate receptor-encoding gene.

As used herein, by "protein" or "polypeptide" is meant any chain of amino acids, regardless of length or post-translational modification (e.g., glycosylation or phosphorylation).

By "neurodegenerative disorder" is meant a disorder which is characterized by the death or loss of function of neuronal cells, also known as neurons. Neuronal death or loss of function can be associated with a number of diseases and syndromes including, without limitation, stroke, epilepsy, Parkinson's disease, Huntington's disease, amyotrophic lateral sclerosis, multiple sclerosis, and Alzheimer's disease.

By "$G\alpha_s$-induced toxicity" is meant the neurodegeneration resulting from expression of the GTP-ase defective $G\alpha_s$ protein.

By "reporter gene" is meant any gene which encodes a product whose expression is detectable. A reporter gene product may have one of the following attributes, without restriction: fluorescence (e.g., green fluorescent protein), enzymatic activity (e.g., lacZ), toxicity (e.g., HER-1), or an ability to be specifically bound by a second molecule (e.g., biotin or a detectably labelled antibody).

By "cAMP regulatory gene" is meant any gene whose product regulates or is regulated by cAMP. Exemplary gene products include ACY-1, UNC-36, and EAT-4. Other preferred cAMP regulatory gene products include the ionotropic (cation) glutamate receptors (iGluRs), the Cl⁻ ionotropic glutamate receptors (GluCls), and the metabotropic glutamate receptors (mGluRs).

By "operably linked" is meant that a gene and a regulatory sequence are connected in such a way as to permit expression of the gene product under the control of the regulatory sequence.

By "purified nucleic acid" is meant DNA that is free of the genes which, in the naturally-occurring genome of the organism from which the DNA of the invention is derived, flank the gene. The term therefore includes, for example, a recombinant DNA which is incorporated into a vector; into an autosomally replicating plasmid or virus; or into the genomic DNA or a prokaryote or eukaryote; or which exists as a separate molecule (e.g., a cDNA or a genomic or cDNA fragment produced by PCR or restriction endonuclease digestion) independent of other sequences. It also includes a recombinant DNA which is part of a hybrid gene encoding additional polypeptide sequence.

By a "transgene" is meant a nucleic acid sequence which is inserted by artifice into a cell and becomes a part of the genome of that cell and its progeny. Such a transgene may be partly or entirely heterologous to the cell.

By "mammalian eat-4 polypeptide or mammalian EAT-4" is meant an amino acid sequence derived from a mammalian cell which shares at least 50%, preferably 70%, more preferably 80%, and most preferably 90% amino acid sequence identity with a C. elegans eat-4 amino acid sequence (SEQ ID NO: 1). Preferably, such a polypeptide is capable of at least partially complementing a C. elegans eat-4 mutation.

By "acy-1 polypeptide or ACY-1" is meant an amino acid sequence which is substantially identical to the amino acid sequence provided in FIG. 5 (SEQ ID NO: 2).

By "substantially identical" is meant an amino acid sequence or nucleic acid sequence which shares identity with another of the same class. Preferably, such a sequence is at least 85%, more preferably 90%, and most preferably 95% identical to the sequence described in the references provided herein. For polypeptides, the length of comparison sequences will generally be at least 15 amino acids, preferably at least 20 amino acids, more preferably at least 25 amino acids, and most preferably at least 35 amino acids. For nucleic acids, the length of comparison sequences will be at least 45 nucleotides, preferably at least 60 nucleotides, more preferably at least 75 nucleotides, and most preferably at least 105 nucleotides. Identity is typically measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of identity to various substitutions, deletions, substitutions, and other modifications.

Other features and advantages of the invention will be apparent from the following detailed description thereof, and from the claims.

BRIEF DESCRIPTION OF THE DRAWINGS

FIG. 2 is a table listing the extent of swelling and cytotoxicity of PVC neurons resulting from the expression of the $\alpha_s(gf)$ transgene in various genetic backgrounds. Statistical differences between genotypes were determined by the method of attributable risk described in J. Devore, Probability and statistics for engineering and the sciences (Brooks/Cole, Belmont, ed. second, 1987). Multiple comparisons were compensated for by setting $p<0.005$ as the threshold for significance.

FIG. 3 is an amino acid sequence of the EAT-4 protein (SEQ ID NO: 1).

FIG. 6 is an amino acid sequence of the ACY-1 protein (SEQ ID NO: 2). The ACY-1 sequence (top) is shown aligned with the mouse adenylyl cyclase type 9 amino acid sequence (bottom) SEQ ID NO: 3) . Underlined sequences indicate predicted transmembrane domains. Positions of the acy-1mutations nu327, nu343, and nu329 are indicated.

DETAILED DESCRIPTION OF THE INVENTION

The invention described herein is based upon genetic studies of the nematode, *Caenorhabditis elegans*. Constitutive activation of the GTP-binding protein $G\alpha_s$ was found to induce neurodegeneration. A screen for mutations that blocked $G\alpha_s$-induced killing identified a gene, acy-1, which encodes a protein that is highly similar (40% identical) to mammalian adenylyl cyclases, indicating that $G\alpha_s$-induced neurotoxicity is likely mediated by changes in cyclic adenosine monophosphate (cAMP) levels. This discovery enables methods and reagents for diagnosing and treating neurodegeneration.

$G\alpha_s$-induced neurotoxicity

Although neurodegeneration is a major feature in a variety of human neurological disorders, relatively little is known about the signal transduction pathways that lead to neurotoxicity, nor how these pathways could be manipulated to protect against neuron loss in these diseases. Two critical questions in the pathogenesis of human neurodegenerative disorders are (1) what factors predispose particular neurons to undergo degeneration and (2) what is the biochemical mechanism of degeneration. A genetic model for excitotoxicity in the nematode *Caenorhabditis elegans* was developed to address these questions.

In particular, a rat cDNA encoding a GTPase-defective (Q227L) $G\alpha_s$ subunit, hereafter referred to as $\alpha_s(gf)$, was expressed in *C. elegans* neurons using the glr-1 glutamate receptor (GluR) promoter. The expression vector, KP#20, was constructed by inserting into a derivative of the *C. elegans* glr-1 expression vector CX#1 (as described in Chalfie et al., Science 263: 802–805, 1994), a 1.5 kb NcoI-XhoI fragment encoding a GTPase defective (Q227L, KP#20) mutant rat $G\alpha_s$ cDNA. *C. elegans* transgenic for $\alpha_s(gf)$ were prepared by microinjecting the KP#20 expression construct together with a glr-1::gfp plasmid (the KP#6 vector) using lin-15 (Huang et al., Mol. Biol. Cell. 5, 395–412, 1994) as a transformation marker. A stable line carrying glr-1 expression constructs for both GFP and the GTPase defective $G\alpha_s$(nuIs5) was isolated following 3500 rads of γ-irradiation. The glr-1 promoter was chosen because it is highly expressed, and because glr-1-expressing cells control locomotion, an easily assayed behavior. The glr-1 promoter is expressed in 17 classes of neurons, including the interneurons (AVB, PVD, AVA, and AVD) required for locomotion. The glr-1 expressing neurons are as follows: AVG, AVJ, DVC, PVC, PVQ, RIG, RIS, RMD, RMEL/R, SMD, URY, as well as the six ASH synaptic targets AIB, AVA, AVB, AVD, AVE, and RIM (Hart et al., Nature 378: 82–85, 1995; Maricq et al., Nature 378: 78–81, 1995).

Figure 1A:
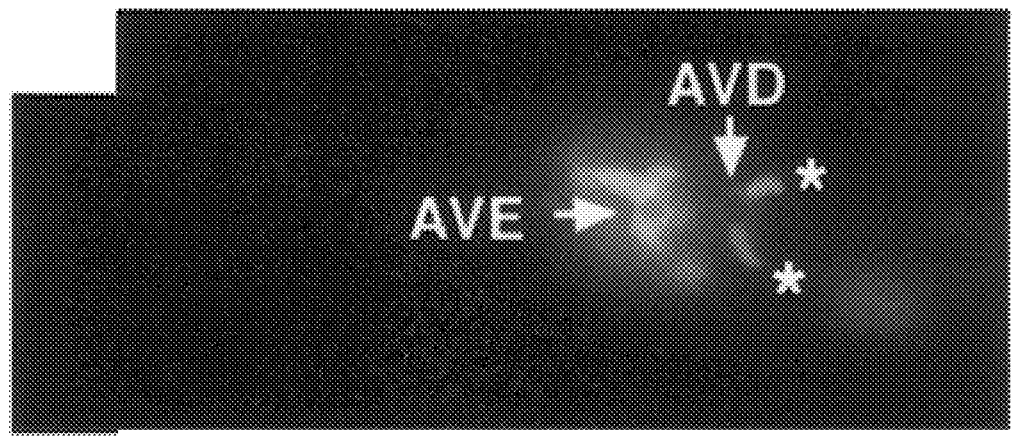
FIGS. 1A and 1B are photographs of neuronal cells from young *Caenorhabditis elegans* larvae co-expressing green fluorescent protein (GFP) with GTP-ase defective rat $G\alpha_s$ as seen morphologically (FIG. 1A), as well as in bright field optics (FIG. 1B).
Figure 1B:
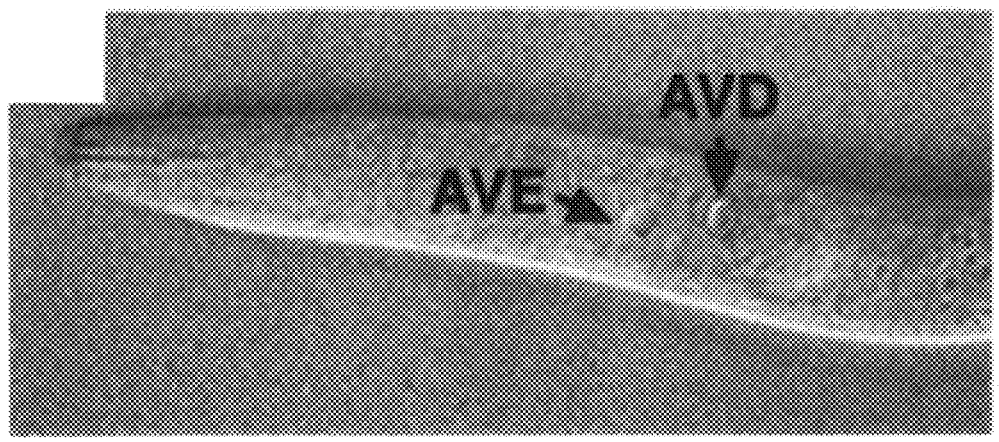

Since $G\alpha_s$ was co-expressed with the green fluorescent protein (GFP) of Aequorea (Chalfie et al., supra), examination of the morphology of $G\alpha_s$-expressing cells was possible. Transgenic glr-1::$\alpha_s(gf)$ animals were found to be paralyzed. As shown in FIGS. 1A and 1B, a subset of the $G\alpha_s$-expressing neurons in young larvae swelled to several times their normal diameter. The swelling was apparent by the morphology of GFP expressing cells (FIG. 1A) and by their appearance in bright field optics (FIG. 1B) as enlarged, apparently vacuolated cells often with an intact nucleus. The interneurons AVE and AVD were swollen compared to neighboring unaffected cells which have been marked in FIGS. 1A and 1B with asterisks. 88% of the PVC neurons swelled, 5% of RIG neurons swelled, and none of the URY cells swelled in first stage (LI) glr-1::$\alpha_s$(gf) larvae. The neurotoxicity occurred in two phases; subsequent to swelling, the swollen cells eventually disappeared, presumably because the cells had died. In glr-1::$\alpha_s$(gf) animals, 89% of the PVC neurons degenerated, as summarized in the table in FIG. 2. Other glr-1 expressing cells degenerated at lower frequencies, including AVA, AVD, AVE, AVG, PVQ, RIG, and SMD. Expression of a constitutively active rat $G\alpha_s$ cDNA was found to cause neurotoxicity in *C. elegans*. Characterization of the neurodegenerative phenotype in the resulting glr-1::$\alpha_s$(gf) was made as follows: Swollen or missing cells were identified by examining the morphology of GFP-expressing cells. $G\alpha_s$-induced neurotoxicity in various genetic backgrounds was quantitated as the number of swollen PVC neurons in L1 larvae, and the percentage of PVC neurons that were missing or swollen in adults hermaphrodites. These results suggested that exaggerated $G\alpha_s$ signaling killed neurons.

The phenotype of $G\alpha_s$-induced neurotoxicity was identical to the neurotoxicity due to excessive signaling by the excitatory neurotransmitter glutamate, which has been termed excitotoxicity. Excitotoxic neuron loss occurs in two phases. First, acute neuron loss is associated with swelling of cell bodies and is dependent on extracellular ionic conditions. Cell swelling is the consequence of depolarization of membrane potential by excitotoxic agonists, which leads to the influx of $Na^+$ and $Cl^-$ [31] ions, and water (Olney, Adv. Exp. Med. Biol. 203: 631–645, 1986; Choi, J. Neurosci. 7: 369–379, 1987; Choi, Neuron 1: 623–634, 1988). Second, delayed neuron loss in excitotoxicity is not dependent on the extracellular ionic conditions, but is correlated with elevations of intracellular $Ca^{2+}$ and chronic activation of immediate early genes (e.g., fos and jun) (Smeyne et al., Nature 363: 166–169, 1993). Hence, $G\alpha_s$-induced neurotoxicity is most likely excitotoxicity.

Neurons Differed Greatly in Their Susceptibility to $G\alpha_s$-induced Toxicity The mec-7 gene product, MEC-7 tubulin, is abundantly expressed in 5 neurons, called touch cells, that sense light touch to the worm's body (Savage et al., Genes Dev. 3: 870–81, 1989; Hamelin et al., EMBO 11: 2885–2893, 1992; Mitani et al., Development 119: 773–783, 1993). To further investigate the specificity of $G\alpha_s$-induced toxicity, $\alpha_s$(gf) was expressed in *C. elegans* utilizing the mec-7 promoter. The mec-7::$\alpha_s$(gf) expression plasmid (KP#7) was constructed by ligating the 1.5 kb NcoI-XhoI $G\alpha_s$(Q227L) into the mec-7 expression vector pPD52.102. *C. elegans* transgenic for the mec-7::$\alpha_s$(gf) expression plasmid were prepared by microinjecting the KP#7 expression construct together with a mec7::gfp plasmid using lin-15 (Huang et al., supra) as a transformation marker. A stable line carrying mec-7 expression constructs for both GFP and the GTPase defective $G\alpha_s$(nuIs5) was isolated following γ-irradiation.

*C. elegans* expressing the mec-7::$\alpha_s$(gf) transgene were found to be indistinguishable from wild type animals, having no obvious defect in touch sensitivity nor in the morphology of the touch cells. Hence, the effects of $G\alpha_s$ on neural activity and on neurotoxicity were cell type specific.

Mutations that Blocked $G\alpha_s$-induced Neurotoxicity

Figure 4:
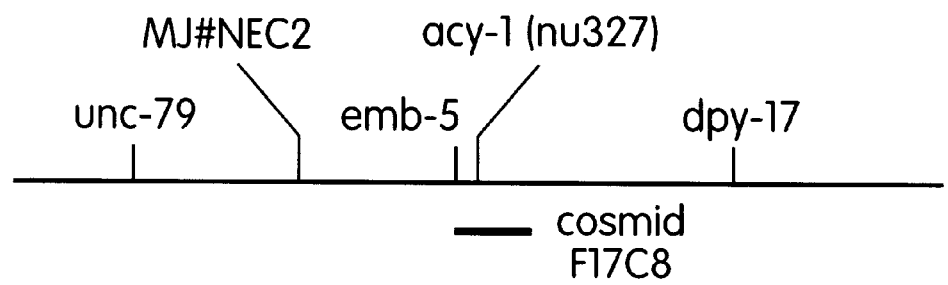
FIG. 4 is a schematic diagram showing the genetic and physical map position of the acy-1 gene on the F17C8 cosmid.

Both the glr-1 and the mec-7 expression constructs supported the notion that the effects of $G\alpha_s$ on neural activity and on neurotoxicity were cell type specific. Since the mec-7 promoter is very highly expressed in the touch neurons (Savage et al., supra; Hamelin et al., supra; Mitani et al., supra), the results also suggested that the cell type specificity could not be overcome by high levels of $G\alpha_s$ expression. To identify the targets of $G\alpha_s$, mutations that block $G\alpha_s$-induced paralysis and neurotoxicity were isolated by identifying mutations isolated from the F2 self-progeny of EMS mutagenized (5 μl/ml) hermaphrodites that restored normal locomotion rates to $\alpha_s$(gf) homozygotes. Candidate suppressor mutants (7500 hapliod genomes) were subsequently screened for reduction of $G\alpha_s$-induced swelling in L1 larvae which led to the isolation of 3 semidominant mutations which blocked $G\alpha_s$-induced paralysis and neurotoxicity Mutations in acy-1 Blocked $G\alpha_s$-induced Neurotoxicity In two factor mapping experiments, the three mutations that blocked $G\alpha_s$-induced neurotoxicity were all found to be linked to dpy-17. Three factor mapping placed these mutations between emb-5 and dpy-17: (nu327 dpy-7) 37/37 unc-32; (nu329 dpy-17) 16/16 unc-32; (nu343 dpy-17) 4/4 unc-32; unc-79 (6/14) MJ#NEC2 (5/14) nu329 (3/14) dpy-17; emb-5 (1/16) nu327 (15/16) dpy-17. As illustrated in the schematic diagram of FIG. 4, two of the three mutations were mapped to a 1.5 cM genetic interval between MJ#NEC2 and dpy-17 on the F17C8 cosmid. The cosmid was then microinjected into acy-1(nu327); nuIs5 animals, and transgenic lines were isolated using goa-1::gfp (KP#13) (Segalat, et al., Science 267, 1648–1651, 1995) as a transformation marker. Four independent lines carrying a cosmid from this interval (F17C8) were obtained, two of which corrected the mutant phenotype of acy-1(nu327) animals, i.e., they had increased degeneration of the PVC neurons. This is shown on Table 1.

TABLE 1

Transgenes containing the F17C8 cosmid rescue the acy-1(nu327) mutant phenotype

| genotype | % PVC degeneration |
|---|---|
| acy-1(nu327);$\alpha_s$(gf) | 12 |
| acy-1(nu327);$\alpha_s$(gf); nuEX(F17C8) | 75 |
| $\alpha_s$(gf) | 88 |

Figure 5:
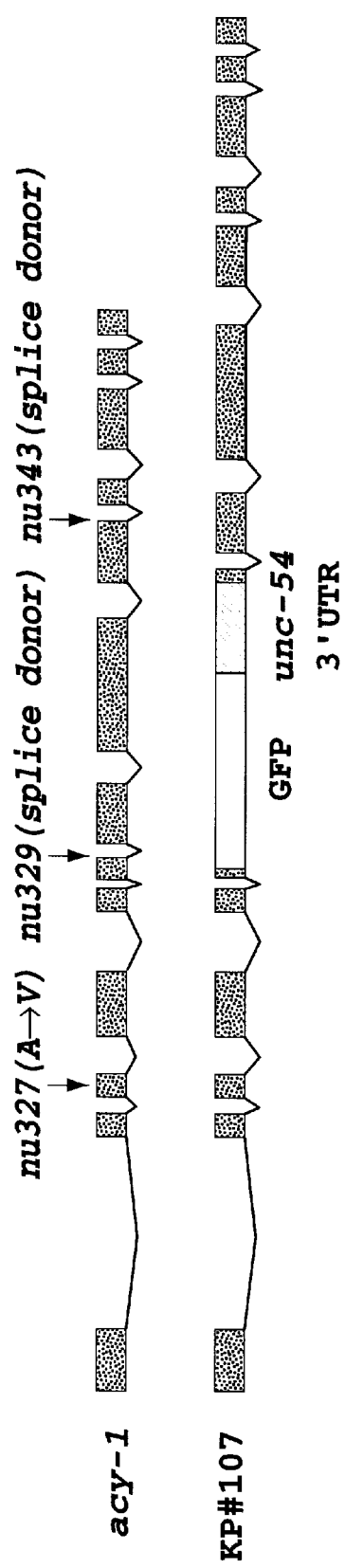
FIG. 5 is a set of schematic diagrams of the predicted structures of the acy-1 gene and the GFP fusion protein (KP#107). Positions of the acy-1 mutations nu327, nu343, and nu329 are indicated.
Figure 7A:
FIGS. 7A and 7B are photographs of GFP-expressing PVC neurons in adult $\alpha_s(gf)$ (FIG. 7A) and adult $\alpha_s(gf)$;acy-1(nu343) (FIG. 7B) C. elegans.
Figure 7B:
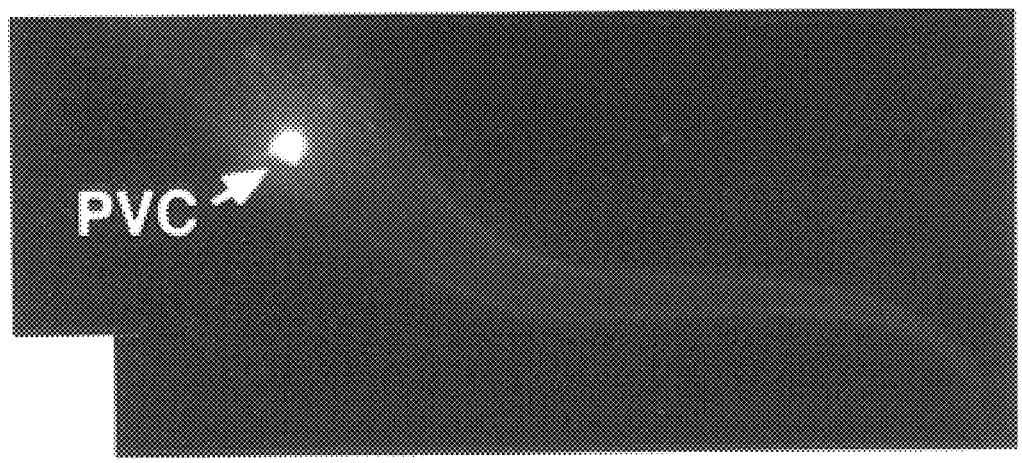

In addition, FIG. 5 shows that all three alleles corresponded to mutations in the predicted exons of the gene F17C8.1, one of two predicted adenylyl cyclase genes in the C. elegans genome database. This adenylyl cyclase gene has been named acy-1. Furthermore, FIG. 6 shows the results of a Genbank database scan for sequences related to acy-1 (SEQ ID NO: 2). The amino acid sequence of ACY-1 was found to be 40% identical at the amino acid level to mouse adenylyl cyclase type 9. It is unclear why the acy-1 mutations were partially dominant. Analysis of the molecular nature of the mutations suggested that they were simple loss of function mutations. For example, nu329 and nu343 were predicted to disrupt pre-mRNA splicing. Indeed, as is shown in FIGS. 7A and 7B, the GFP-expressing PVC neurons which were typically missing in $\alpha_s$(gf) adult transgenic worms (FIG. 7A) were present in $\alpha_s$(gf);acy-1(nu343) (FIG. 7B). Thus, it is possible that $\alpha_s$(gf) animals were highly sensitive to changes in cAMP levels. Overall, the results suggested that G$\alpha_s$ neurotoxicity was mediated by changes in intracellular cAMP.

Physiological Function of ACY-1

To determine the physiological function of ACY-1, an analysis of acy-1 expression was carried out. A deleted derivative (KP#106) of the cosmid F17C8 was isolated by digesting with AfiII and re-ligating. KP#106 contained the entire 8.35 kb acy-1 genomic region together with the 5.2 kb 5' and 4.9 kb 3' flanking sequences. An acy-1::gfp expression vector (KP#107) was constructed by PCR amplification of a 1.7 kb fragment containing the GFP coding region and the unc-54 transcription terminator from pPD95.75, followed by ligation of this fragment into the unique Asp718 site in KP#106, creating a fusion protein containing the first 6 exons of acy-1 fused to GFP. The ACY-1::GFP fusion protein contained 6 predicted transmembrane domains of ACY-1, and was therefore membrane localized. Transgenic animals carrying KP#107 were isolated by microinjection using lin-15 (Huang et al., supra) as a transformation marker. Expressing cells were identified based on their morphology and nuclear positions.

Figure 8A:
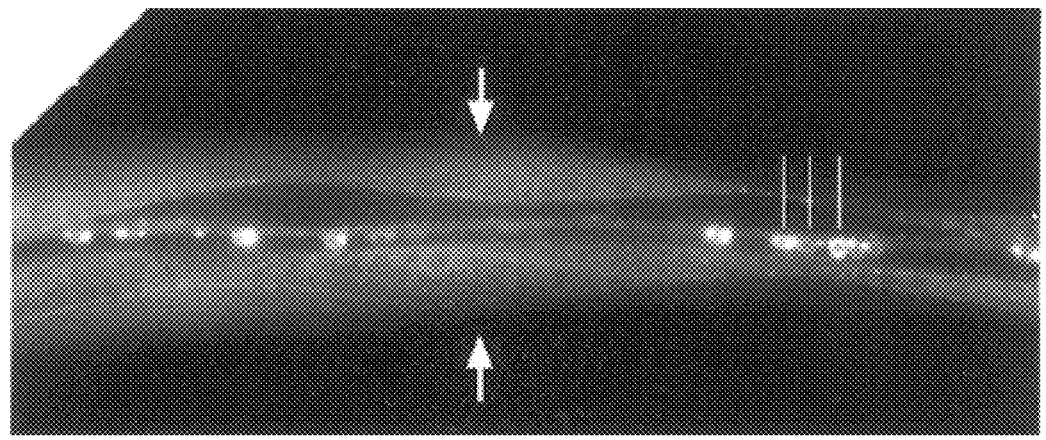
FIGS. 8A and 8B are photographs illustrating KP#107 acy-1::gfp fusion gene expression in neurons (FIG. 8A) and muscle (FIG. 8B).
Figure 8B:
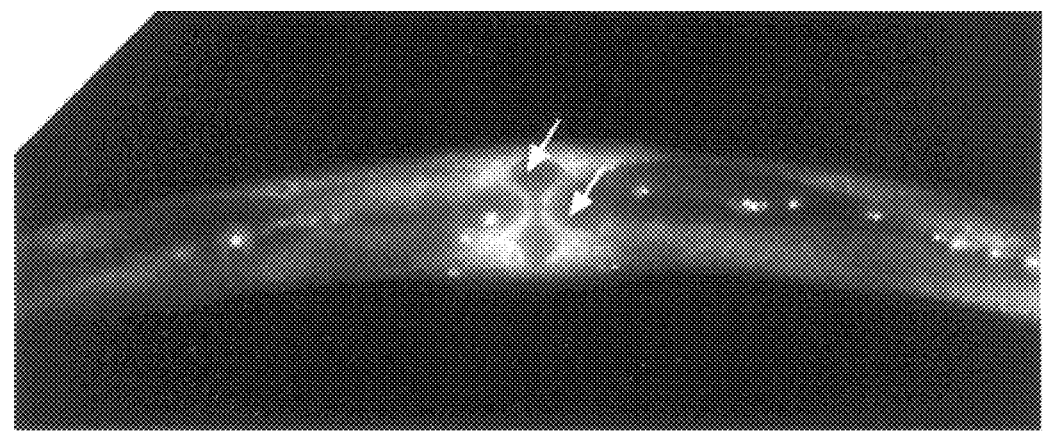

The expression pattern of acy-1 was determined by analyzing the GFP reporter construct. As is shown in FIGS. 8A and 8B, the acy-1::gfp fusion protein was expressed in virtually all neurons (FIG. 8A) and body muscles (FIG. 8B). In FIG. 8A, ACY-1 expression in the two ventral rows of body muscles (arrows) and in the ventral cord neurons and neuropile (lines) is shown. In FIG. 8B, expression of ACY-1 in the vulva muscles (arrow heads) is shown. Nearly all of the 302 neurons in adult C. elegans appeared to express ACY-1. Cell bodies were identified based upon the bright fluorescence in the intracellular membranes (which are presumably the endoplasmic reticulum of Golgi apparatus). ACY-1 did not appear to be expressed in non-neural tissues or in the pharynx. These results indicated that the ACY-1 adenylyl cyclase is likely to participate in many neural signaling pathways. Therefore, we expected that acy-1 mutants would have defects in behavior or development. Consistent with this notion is that mutations which inactivated the C. elegans G$\alpha_s$ subunit (GSA-1) were found to be homozygous lethal. Surprisingly, we observed that acy-1 homozygotes were nearly indistinguishable from wild type animals. This result suggested that the essential function of GSA-1 was mediated by some other adenylyl cyclase. Alternatively, acy-1 and other adenylyl cyclases could act redundantly in the essential GSA-1 pathways.

Activated G$\alpha_s$ Induced Neurotoxicity by Excitotoxicity

Several previously identified genes were considered good candidates for mediating the toxic effects of G$\alpha_s$. Two cyclic nucleotide gated ion channel (CNGC) subunit genes tax-2 and tax-4 (Coburn and Bargmann, Neuron 17: 695–706, 1996; Komatsu et al., Neuron 17: 707–718, 1996) are not expressed in glr-1 expressing cells and hence are unlikely targets. The mec-6, unc-8, and deg-1 genes have been previously implicated in neurodegeneration (Chalfie and Wolinksy, Nature 345: 410–416 (1990); Driscoll and Chalfie, Nature 349: 588–593 ,1991; Shreffler et al., Genetics 139: 1261–1272, 1995; Tavernarakis et al., Neuron 18: 107–119, 1997), and the DEG-1 and UNC-8 proteins are similar to mammalian epithelial sodium channel subunits (ENaC), which are potently activated by cAMP-dependent protein kinase (PKA) (Sariban-Sohraby et al., J. Biol. Chem. 263: 13875–13879, 1988; Oh et al., Am. J. Physiol. 265: C85–C91, 1993; Bubien et al., J. Biol. Chem. 269: 17780–17783, 1994). The unc-2, unc-36, and egl-19 genes encode subunits of voltage-dependent $Ca^{2+}$-channels (Schafer and Kenyon, Nature 375: 73–78, 1995) which are likely to be regulated by PKA (Curtis and Catterall, Proc. Nati. Acad. Sci. USA 82: 2528–2532, 1985) and have also been implicated in neurodegeneration. The glr-1 gene encodes an ionotropic GluR (Hart et al., supra; Maricq et al., supra). GluRs have been implicated in neurotoxicity in mammals (Olney, Adv. Exp. Med. Biol. 203, 631–645, 1986; Choi, J., Neurosci. 7: 369–379, 1987; and Choi, Neuron 1, 623–634, 1988), and PKA augments the response of mammalian neurons to glutamatergic agonists (Greengard et al., Science 253: 1135–1138, 1991).

To examine the above genes for a possible role in G$\alpha_s$ induced toxicity, the neurodegenerative phenotype was characterized as described above. As shown in FIG. 2, of the candidate genes, only the unc-36 mutation significantly reduced G$\alpha_s$-induced cytotoxicity. Interestingly, the unc-36 mutation had no effect on cell swelling. Since UNC-36 $Ca^{2+}$ channels were required for cytotoxicity, these results suggested that G$\alpha_s$ cytotoxicity was mediated in part by either $Ca^{2+}$ influx or depolarization of the affected cells. All other candidate genes had no effect on either neuron swelling or deaths in glr-1::$\alpha_s$(gf) animals. Our results do not exclude the possibility that these other candidate PKA targets also play a role in G$\alpha_s$-induced toxicity. For example, more than one type of channel may be capable of mediating the toxic effects of G$\alpha_s$ in which case neurotoxicity would be prevented only in multiply mutant animals.

The glr-1 Mutation was Unlikely to Completely Abolish Glutamate Signaling in vivo Given its role in excitotoxicity in mammals, the requirement of endogenous glutamate signaling for G$\alpha_s$ neurotoxicity was tested. Although the glr-1 mutation was not neuroprotective, it was possible that cAMP toxicity was mediated by exaggerated responses to endogenous glutamate. The C. elegans genome sequence (currently ~70% complete) predicted six additional ionotropic GluR subunits; therefore, the glr-1 mutation was unlikely to completely abolish glutamate signaling in vivo.

Eat-4 Mutant Alleles Eliminated ASH-mediated Touch Sensitivity

Prior work had shown that ASH sensory neurons mediated an aversive response to three distinct stimuli (nose touch, osmotic shock, and volatile repellents), and that the ASH-mediated touch response required functional GLR-1 glutamate receptors in synaptic targets of ASH (Hart et al., supra; Maricq et al., supra; Kaplan and Horovitz, Proc. Natl. Acad. Sci. (USA) 90, 2227–2231, 1993; Troemel et al., Cell 83, 207–218,1995). Hence, genes required for ASH sensory responses were tested for their ability to perturb glutamate signaling.

We screened 11,000 mutagenized haploid genomes for animals that failed to respond to nose touch. Mutants isolated were subjected to a series of secondary screens, including dye-filling of the amphid sensory neurons, and responsiveness to osmotic shock and volatile repellents. Seven alleles of eat-4 were isolated in this screen, all of which were normal for dye-filling but were defective for all three ASH sensory behaviors. The amino acid sequence of the EAT-4 is shown on FIG. 3. ASH-mediated sensory responses to nose touch, osmotic shock, and volatile repellents were compared in wild type and eat-4, as has been previously described (Hart et al., supra; Maricq et al, supra; Kaplan and Horovitz, supra; Troemel et al., supra). Briefly, for nose touch, animals were tested 10 times each with a positive response being scored when animals either halted forward movement or initiated backward movement following the stimulus. For osmotic avoidance, 50–60 animals were placed in 1 cm rings formed with 8 M glycerol, and the number of animals that escaped the ring after 9 minutes were counted. For volatile avoidance, an eyelash was dipped in 1-octanol and held near an animal's nose, and responses were quantitated by recording the length of time that elapsed before the animals reversed locomotion.

All seven eat-4 strains isolated had similar behavioral defects. In particular, as is portrayed in Table 2, eat-4 strains had severe defects in the ASH-mediated touch, osmosensory, and volatile repellent responses.

TABLE 2

Role of eat-4 in ASH sensory responses

| Genotype: | Nose Touch (% Respond) | Osmotic Avoidance (% Escape) | Volatile Avoidance (seconds) |
|---|---|---|---|
| wild type | 86 +/− 3 | 2 +/− 1 | 2.9 +/− 0.9 |
| eat-4(ky5) | 1 +/− 1 | 75 +/− 6 | 9.9 +/− 1.6 |
| eat-4(n2474) | 2 +/− 1 | 54 +/− 6 | 9.6 +/− 1.5 |

Errors indicate standard error of the mean in all cases. The number of animals and trials for each genotype were as follows: for nose touch, 10 animals and 100 trials; for osmotic avoidance, 60 animals and 5 trials; and for volatile avoidance, 25 animals and 25 trials.

Eat-4 Mutations Reduced $G\alpha_s$-induced Cytotoxicity but Not Cell Swelling

The eat-4 gene was initially identified in screens for mutations that disrupted eating behavior (Avery, Genetics 133: 897–917, 1993). The eat-4 eating defect was caused by elimination of a glutamate-induced inhibitory synaptic signal (mediated by the M3 motor neuron), which could be observed in extracellular recordings of pharyngeal muscle activity (Raizen et al., Neuron 12, 483–495, 1994). Given the results described herein, the eating defects and the ASH sensory defects could both be explained by an underlying defect in glutamate signaling.

To investigate this possibility, neurodegenerative phenotypes were examined as described above. In these experiments, eat-4 mutations were found to be neuroprotective. The mutations significantly reduced $G\alpha_s$-induced cytotoxicity but had no apparent effect on cell swelling, as indicated in FIG. 2. In addition to reducing cytotoxicity, the eat-4 mutations also dramatically improved the locomotion rate of $\alpha_s(gf)$ animals. These results suggested that $G\alpha_s$ neurotoxicity was at least partially mediated by endogenous glutamate signaling.

Apoptosis Was Not Required for $G\alpha_s$ Neurotoxicity

Apoptosis is a naturally occurring process thought to play a critical role in the developing animal and is characterized morphologically by condensation of the chromatin followed by shrinkage of the cell body. Biochemically, DNA laddering, the degradation of nuclear DNA into oligonucleosomal fragments, is the hallmark of apoptosis. DNA laddering precedes cell death. Apoptosis is most likely dependent upon the activation of a cell death pathway. The best defined genetic pathway of cell death is in C. elegans where both effector (ced-3 and ced-4) and repressor (ced-9) genes have been isolated. Similar genes have been identified in mammals. Whether excitotoxic death occurs by apoptosis or by necrosis has remained controversial. This uncertainty is primarily due to lack of genetic control of the apoptosis pathway in the previously described models for excitotoxicity.

Figure 9A:
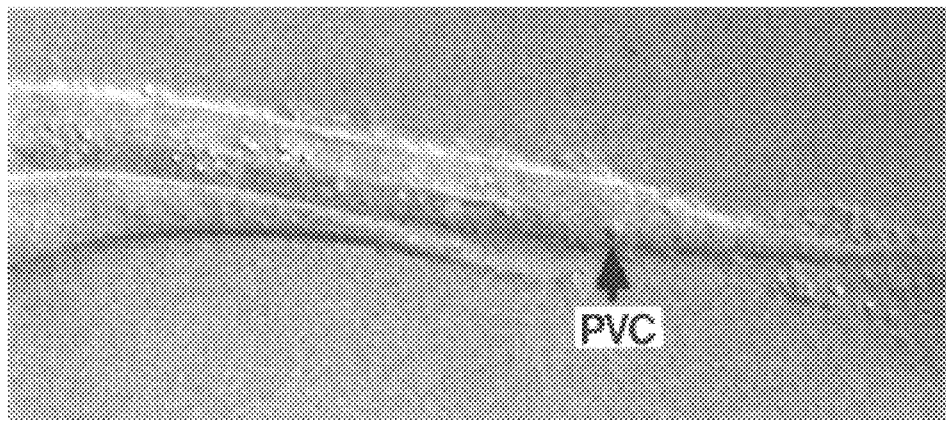
FIGS. 9A and 9B are photographs of PVC neurons from unc-18 L1 larvae as seen with bright field (FIG. 9A) and fluorescence (FIG. 9B) optics.
Figure 9B:
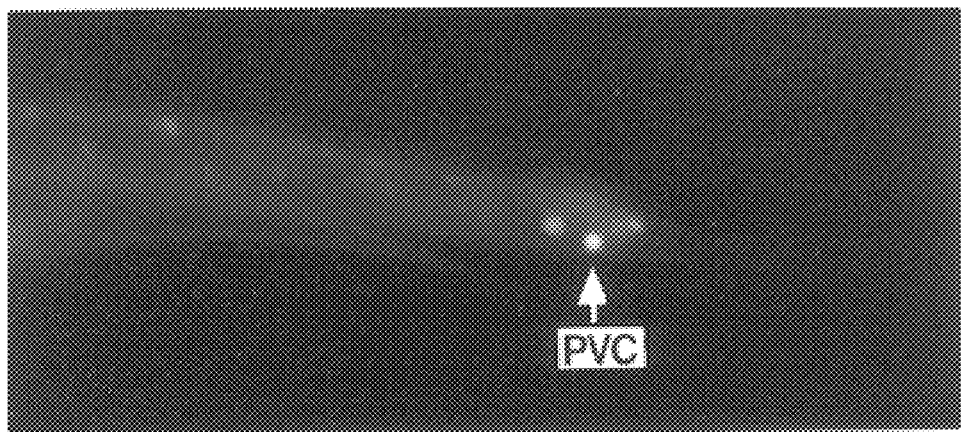
Figure 10A:
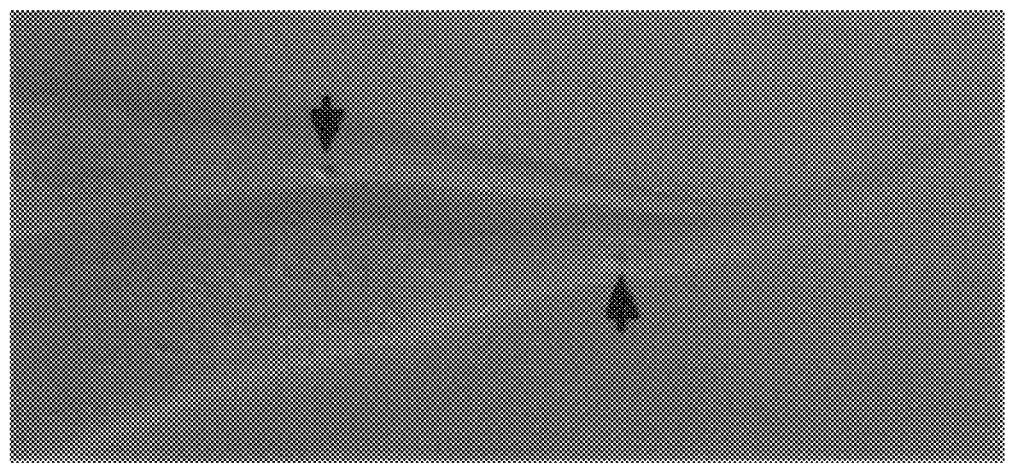
FIGS. 10A and 10B are photographs of PVC neurons from unc-18 adults as seen with bright field (FIG. 10A) and fluorescence (FIG. 10B) optics.
Figure 10B:
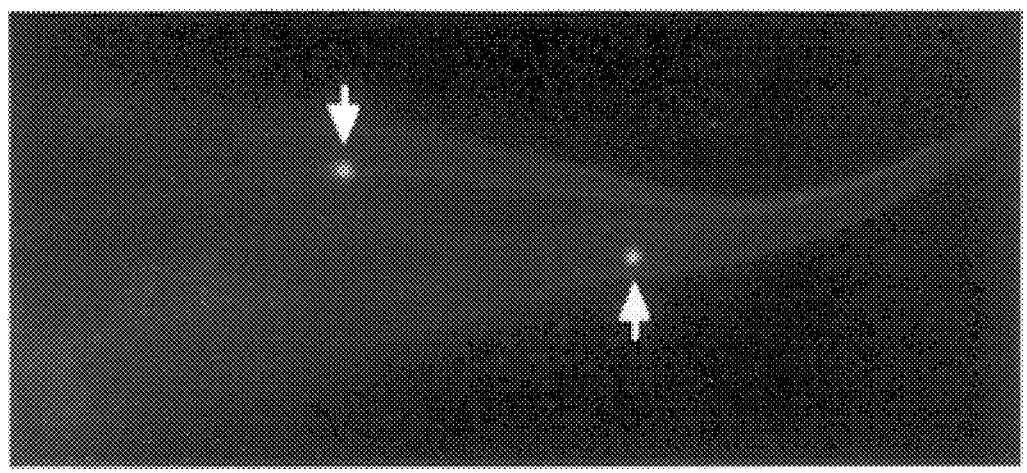

In our experiments, we found that a mutation in the ced-3 gene, which encodes an ICE protease and is required for apoptosis (Ellis and Horovitz, Cell 44: 817–829, 1986; Yuan et al., Cell 75: 641–652, 1993), had no effect on $G\alpha_s$-induced swelling or killing (see FIG. 2). Thus, apoptosis was not required for $G\alpha_s$-induced killing. However, in $\alpha_s(gs)$ ;unc-18 double mutants, a significant fraction of PVC neurons had a highly condensed morphology, and these PVC neuron corpses appeared to be engulfed by surrounding hypodermal cells, both of which are characteristic of apoptotic deaths (Ellis et al., Ann. Rev. Cell Biol. 7: 663–698, 1991). As shown in FIGS. 9A and 9B, in unc-18 L1 larvae, 13% of the PVC neurons exhibit the condensed morphologies characteristic of programmed cell deaths, which was apparent in both bright field (FIG. 9A) and fluorescence (FIG. 9B) optics. In unc-18 adults, 25% of the PVC neurons exhibited condensed morphologies and appeared to have been engulfed by surrounding hypodermal cells in the tail, as shown in FIG. 10A (bright field optics) and FIG. 10B (fluorescence optics). (Note that the position of the indicated cell body in FIG. 10B is much further posterior than in FIG. 7B). $G\alpha_s$ neurotoxicity was concluded to be, in part, mediated by synaptic input to the dying cells, since unc-18 mutations impair synaptic vesicle exocytosis (Gengyo-Ando, et al., Neuron 11: 703–711, 1993; Hata et al., Nature 366: 347–351, 1993). Furthermore, these results suggest that $G\alpha_s$ neurotoxicity occurs via two independent mechanisms. Synaptic input promotes an excitotoxic pattern of cell deaths; however, when synaptic input is impaired an apoptotic pattern emerges.

Screens for Compounds that Inhibit cAMP-based Neurodegeneration

As described herein, constitutive activation of the GTP-binding protein $G\alpha_s$ induces a neurodegeneration phenotype that shares several properties with excitotoxic neuron loss in mammals. First, neuron loss occurs in two phases, whereby affected cells undergo a swelling response in young larvae, and subsequently die sometime during larval development. Second, neurons differ greatly in their susceptibility to $G\alpha_s$-induced toxicity, ranging from 0–88% of cells affected.

Third, a mutation that impairs the function of voltage-dependent calcium channels and one that reduces glutamate neurotransmission are neuroprotective.

The acy-1 gene was identified in a screen for mutations that blocked $G_s$-induced killing and has been positionally cloned. The predicted ACY-1 protein (SEQ ID NO: 2) is highly similar (40% identical) to a mammalian adenylyl cyclase. Most consistent with this result is that $G\alpha_s$-induced neurotoxicity is mediated by changes in cyclic adenosine monophosphate (cAMP) levels. Mutations that prevent programmed cell death, also known as apoptosis, do not prevent $G\alpha_s$-induced neurotoxicity; however, when synaptic transmission was impaired (by an unc-18 mutation), a subset of the deaths appear to become apoptotic. These experiments suggested that excitotoxicity normally occurs by both apoptosis and a second cytotoxic pathway. Given these results, screens for compounds that inhibit cAMP signaling may be carried out to identify drugs that alter cAMP-based neurodegeneration and to provide therapies to ameliorate these disorders in humans and other mammals. These assays may be carried out in vivo or in vitro, and a number of exemplary assays now follow.

a) C. elegans assays

The microscopic nematode, C. elegans, is a useful model for studying neurodegeneration because it allows researchers to observe changes in neuronal cells within the living organisms over the three days required for a C. elegans to develop from a single cell zygote to a mature adult. The biology of the C. elegans nervous system, which includes 302 neurons, has been well documented. Furthermore, there are several similarities between the C. elegans and human nervous systems. For example, many of the C. elegans neurotransmitters are the same as human neurotransmitters. In addition, many C. elegans genes used both inside and outside of the nervous system have counterparts in mammals.

To identify a compound capable of inhibiting cAMP-based neurotoxicity, candidate compounds are screened for an ability to alter cAMP levels using a C. elegans strain carrying a reporter transgene operably linked to a promoter of a gene that is either (i) regulated by cAMP or (ii) involved in cAMP regulation. Exemplary promoters include the acy-1, unc-36, and eat-4 promoters. Other desirable promoters include any promoter from a nematode glutamate receptor (GluR) gene; such genes are listed, for example, in Table 3.

TABLE 3

C. elegans glutamate signalling genes

| Gene Product | | Genetic locus |
|---|---|---|
| iGluRs: | C06E1.4 | glr-1 |
| | CO6A8.8 | |
| | BO280.12 | |
| | F41B4.4 | |
| | C43H6 | |
| | K10D3.1 | |
| | ZC196.c | |
| GluCls: | GluCLα1 | |
| | GluCLβ1 | |
| | ZC317.3 | |
| | T10G3 | |
| mGluRs: | ZC506.4 | mgr-1 |
| | F45H11 | |

Once constructed, a transgenic C. elegans strain carrying such a reporter gene is treated with a candidate compound, or any number of compounds in combination, and animals are screened for alterations in cAMP levels as reflected by alterations in the levels of reporter gene expression.

Useful reporter genes are those whose expression is detectable, preferably, using simple and rapid techniques. Preferable reporter genes include, without limitation, green fluorescent protein (gfp), spectrally shifted green fluorescent proteins (Rizzuto et al., Curr. Biol. 6:183–188, 1996; Heim and Tsien, Curr. Biol. 6:178–182, 1996); lacZ, her1 (Perry et al., Gen. and Dev. 7(2): 216–228, 1993), and mec4 (dominant) (Maricq et al., supra). Expression levels of these reporter genes may be directly measured by a variety of techniques known in the art. For example, if the reporter protein is a toxin (e.g., MEC4), the expression level may be detected by measuring or observing cell viability. The expression level of a reporter protein with enzymatic activity (e.g., lacZ) may be quantitated using colorimetric substrates (e.g., 5-bromo-4-chloro-3-indolyl-β-D-galactoside (X-Gal)). And reporter gene products such as GFP may be screened directly by visual inspection.

If desired, reporter proteins may be fusion proteins that incorporate portions of the sequences involved in cAMP regulation, for example, the ACY-1, UNC-36, or EAT-4 sequences. These fusion proteins are generated using nucleotide sequences and methods known in the art and described herein.

In one particular embodiment, such compound screens are carried out using rapid, high through-put assays. For example, transgenic C. elegans animals carrying acy-1::gfp reporter constructs are utilized. The animals are distributed into 96-well microtiter dishes such that there is one animal per well. Candidate compounds are then individually or combinatorially added to the wells and assessed for an ability to reduce GFP expression as a means to test for an ability to inhibit cAMP-based neurodegeneration. GFP assays may be carried out by any means, but are preferably monitored using a microtiter plate fluorescence reader.

In an alternative compound screen, the reporter protein need not be GFP. For example, the transgenic animal may carry a lacZ reporter gene and be distributed into microtiter wells as described above. Following compound administration, transgenic animals are subjected to standard β-galactosidase activity assays described in the art (see, for example, Ausubel et al., supra). The Promega β-gactosidase enzyme assay system with reporter gene lysis buffer kit (Catalog # E2000) may be employed in this rapid high throughput 96 well assay system. By this method, reporter lysis buffer is added to each well. The C. elegans extracts are then incubated with the buffer and the o-nitrophenyl-β-D-glactopyranoside (OPTG) substrate provided in the kit. Optical density of the plate is then measured on a microtiter plate reader. Again, a reduced level of lacZ activity in a compound-treated well as compared to an untreated well indicates that the compound has an ability to inhibit cAMP-based neurodegeneration.

In addition, a variety of methods may be used in combination to screen for compounds capable of inhibiting cAMP-based neurodegeneration. For example, a C. elegans carrying two different expression constructs (e.g., the acy-1 promoter operably linked to gfp and the glr-1 promoter operably linked to lacZ) may be used to screen for a compound capable of inhibiting cAMP-based neurodegeneration by assaying for a reduction in the expression of both the acy-1 and eat-4 genes. In this assay, preferred compounds are capable of reducing the expression levels of both GFP and lacZ. However, a decrease in expression of one reporter gene (e.g., gfp), but not the other reporter gene (e.g., lacZ) identifies compounds capable of targeting particular components in a neurodegenerative pathway (in this case, the acy-1 gene). Such compounds may be useful for treating particular types of neurodegenerative disorders.

In addition, nematode screens for compounds capable of inhibiting cAMP-based neurodegeneration may be based upon both neuroprotection and reporter gene expression. By this approach, for example, a transgenic glr-1::$\alpha_s$(gf) *C. elegans* is transformed with a second worm marker (e.g., the acy-1::gfp expression vector). Compound-treated glr-1::$\alpha_s$ (gf); acy-1::gfp double transgenic animals are then screened, for example, for improved locomotion (i.e., a compound affecting the glr-1 gene), reduction of GFP expression (i.e., a compound affecting the acy-1 gene), or both (i.e., a compound affecting both the glr-1 and acy-1 genes) as compared to untreated glr-1::$\alpha_s$(gf); acy-1::gfp double trangenic animals. Again, gene-specific compounds may be useful for treating neurodegenerative disorders involving specific genes.

In yet another approach, compounds which affect neurodegenerative signals generated by a mammalian glutamate receptor may also be employed in a *C. elegans* screen. A large number of mammalian glutamate receptors (GluRs) have been previously described, and a comprehensive list of these proteins may be found in Hollmann and Heinemann (Ann. Rev. Neurosci. 17: 31–108, 1994). To carry out such a screen, the coding regions of one or more of these genes are inserted into a *C. elegans* expression vector such that the expression of the gene product is directed by the glr-1 gene promoter. This construct is microinjected into a glr::$\alpha_s$(gf) transgenic *C. elegans*. Since only a subset of the glr-1 expressing neurons die in such animals, any additional cell death (as measured, for example, by increased paralysis, neuronal swelling, or neurodegeneration) may be attributed to mammalian GluR expression. Candidate compounds are then administered to these animals, and differences observed in compound-treated animals versus untreated animals are used to identify a compound having an ability to affect mammalian GluR signalling. Again, compounds identified by this assay are useful for treating neurodegenerative disorders in a mammal.

b) Mammalian Cell Assays

Mammalian cells carrying a reporter gene operably linked to a gene either regulated by cAMP or involved in cAMP regulation, for example, the mammalian homologues of the acy-1, unc-36, or eat-4 genes, may also be used to screen for compounds that inhibit cAMP-based neurodegeneration. In one particular example, the promoter of the murine adenylyl cyclase type 9 encoding gene may be used to direct the expression of a reporter (e.g., GFP) in a mammalian expression vector. This vector is transfected into a mammalian cell by any of a number of different transfection methods well known in the art (e.g., electroporation, CaPO$_4$ precipitation, or DEAE-Dextran). Preferably, the mammalian cell is a mouse neuronal cell line, for example, a PC12 cell line. Candidate compounds are added to the culture medium of the transfected cells, and the level of expression of the reporter gene is measured and compared to a control, untreated cell line. A reduced level of reporter gene expression in a compound-treated cell line indicates that the compound has an ability to inhibit cAMP-based neurodegeneration in mammalian cells.

In addition, such a mammalian cell line may be transfected with more than one reporter gene operably linked to more than one cAMP regulatory gene promoter. For example, a mammalian cell transfected with a gfp-adenylyl cyclase type 9 construct may be doubly transfected with a construct comprising a mammalian unc-36 promoter operably linked to a second reporter (e.g., luciferase). Following addition of candidate compounds to the culture medium of doubly transfected cells, GFP expression is analyzed, for example, by flow cytometric analysis of half of the compound-treated cell population, and the remaining half is assayed for luciferase activity using known methods (e.g., the luciferase assay kit commercially available from Promega). By comparing GFP and luciferase expression levels to those in untreated cells, a compound capable of altering cAMP-based neurodegeneration is identified. Furthermore, a compound capable of affecting, for example, the murine adenylyl cyclase type 9 gene but not the mammalian unc-36 gene may also be isolated. Such a compound may be useful for treating specific types of neurodegenerative disorders in mammals.

Alternatively, mammalian cells which endogenously express homologues of *C. elegans* genes involved in cAMP regulation or regulated by cAMP may be used to identify compounds capable of altering cAMP-induced neurodegeneration. According to this method, following administration of a candidate compound, endogenous gene expression is measured by any of a variety of nucleic acid or immunological based assays including, without limitation, Northern blot, Western blot, and ELISA analyses. Compounds affecting endogenous gene expression levels as compared to untreated cells are useful for treating cAMP-based neurodegeneration.

c) Animal Models

A number of animal models exist for the study of neurodegenerative disorders and find use in the screening methods described herein. For example, such models may serve as a system in which to screen candidate compounds being tested de novo for an ability to alter cAMP-based neurodegeneration or as a secondary screen for testing compounds isolated in a *C. elegans*, yeast, or mammalian cell culture assay (for example, those assays described herein). Candidate compounds may be administered to animals prior to neurological damage to assay for an ability to prevent cAMP-based neurodegeneration. Alternatively, candidate compounds may be assessed for an ability to treat cAMP-based neurodegeneration following neurological insult. Animal models may also serve to determine the dosage requirement for an effective compound.

Particularly useful animal models include, without limitation, Parkinson's disease (PD) rat models, which are established by injecting the catecholamine-specific neurotoxin, 6-hydroxydopamine (6-OHDA), into the medial forebrain bundle or the substantia nigra pars compact to achieve a rapid degeneration of the nigrostriatal pathway, or into the striatum to achieve progressive degeneration, as has been described (see, for example Gerlach and Riederer, J. Neural. Transm. 103 (8–9): 987–1041, 1996; Bernard et al., J. Comp. Neurol. 368 (4): 553–568, 1996; Asada et al., Ex. Neurol. 139 (2): 173–187, 1996). Alternatively, rats may be rendered "epileptic" (i.e., induced to suffer brain seizures which often result in neuronal cell death) by administration of a variety of compounds including, for example, intravenous injection of bicuculline (Blennow et al., J. Cereb. Blood Flow Metab. 5: 439–445, 1995) or daily application of low intensity electrical stimulation. Finally, neuronal cell death which often results from stroke-induced ischemia may be mimicked by the 4-vessel occlusion experimental model described by Pulsinelli et al. (Ann. Neurol. 11: 491–498, 1982) and Francis and Pulsinelli (Brain Res. 243: 271–278, 1982).

d) Candidate inhibitors of cAMP-based neurodegeneration

A number of compounds have been shown to affect cAMP levels, and these provide good candidates for inhibitors of neurodegeneration. Such compounds are commercially available (e.g., from Research Biochemicals International) and include, without limitation, agonists of receptors that couple to Gi and inhibit adenylyl cyclases. Alpha 2 adrenergic receptor agonists (including B-HT 920 diHCl and Xylazine HCl), opioid delta receptor agonists (including [D-Ala2, D-Leu5]-enkephalin and [D-Pen2,5]-enkephalin), and D2 dopaminc receptor agonists (including bromocriptine methane sulfonate and Quinelorane 2HCl) all inhibit adenylyl cylcases and may be assessed in screens described herein for an ability to inhibit cAMP-based neurodegeneration.

Therapeutics for Treating Human Neurodegenerative Disorders

A number of human neurological disorders are characterized by a loss of neurons through a degenerative process. Compounds isolated as described above based on their effect on cAMP levels are useful in treating these disorders. In addition, drugs known to lower cAMP levels are also useful therapeutics for treating, preventing, or slowing neurodegeneration. In particular, disorders that may be treated using such compounds include, without limitation, Parkinson's disease, Huntington's disease, Amyotrophic lateral sclerosis (ALS), Alzheimer's disease, multiple sclerosis, epilepsy, and stroke.

Compounds that alter cAMP levels may be administered by any appropriate route. For example, administration may be parenteral, intravenous, intra-arterial, subcutaneous, intramuscular, intracranial, intraorbital, ophthalmic, intraventricular, intracapsular, intraspinal, intracisternal, intraperitoneal, intranasal, aerosol, by suppositories, or by oral administration. Therapeutic formulations may be in the form of liquid solutions or suspensions; for oral administration, formulations may be in the form of tablets or capsules; and for intranasal formulations, in the form of powders, nasal drops, or aerosols.

Methods well known in the art for making formulations are found, for example, in "Remington's Pharmaceutical Sciences." Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

Dosage is determined by standard techniques and is dependent, for example, upon the weight of the mammal and the type or extent of disorder being treated.

Diagnostics for Neurodegenerative Disorders

To determine whether an individual either has or is likely to develop a neurodegenerative disorder, that individual is screened for mutations in genes which are either involved in regulation of cAMP, or are regulated by cAMP, for example, genes encoding the adenylyl cyclases, G proteins, or human homologues of UNC-36 or EAT-4 proteins described herein. Such assays may be carried out by any standard technique including, without limitation, methods involving sequencing or mismatch binding or cleaving assays. In one particular example, a nucleic acid sample derived from the neuronal cells of an individual may be isolated (for example, by PCR amplification), and a cAMP regulatory gene (or a portion thereof) subjected to rapid sequence analysis by automated sequencing techniques using primers generated from sequences described herein and in the art.

Alternatively, an individual who either has or is likely to develop a neurodegenerative disorder may be screened for altered expression of adenylyl cyclases, G proteins, or the human homologues of UNC-36 or EAT-4 proteins, or for an increased level of cellular cAMP, particularly in neuronal cells. Such assays may be carried out, for example, using any standard nucleic acid-based assay (e.g., Northern blot analysis) or immunological assay (e.g., enzyme-linked immunosorbent assay (ELISA)), preferably in a high through-put assay format. In one particular example, neuronal cells obtained from an individual being screened for a neurodegenerative disorder may be isolated and analyzed for the expression of adenylyl cyclases, G proteins, and the human homologues of UNC-36 and EAT-4 proteins by ELISAs using fluorophore-tagged antibodies directed toward these proteins as probes. Individuals incapable of expressing certain proteins may be identified by rapidly assessing the results of these ELISAs in a microtiter plate format.

In particular examples, candidate human genes, for example, those involved in cAMP regulation, are examined for genetic linkage to hereditable forms of neurodegeneration found in humans or, as a model system, mice. These genetic linkages are assessed using standard methods known in the art, and, upon identification of a linkage with neurodegeneration, diagnostic mutation detection is conducted as described herein. Listed in Table 4 are exemplary candidate human genes likely involved in neurodegeneration.

TABLE 4

Candidate Human Neurodegeneration Genes

| Class of Protein | Gene Product |
| --- | --- |
| Phosphodiesterases | PDE4A |
|  | PDE4B |
|  | PDE6G |
|  | PDE7A |
| G alpha subunits | GNAS1 |
|  | GNAI1 |
|  | GNAI2 |
|  | GNAI3 |
|  | Golf |
| Protein Phosphatases | PPP1CB |
|  | PPP1CC |
|  | PPP2CA |
|  | PPP2R4 |
|  | PPP2R5A |
|  | PPP2R5C |
|  | PPP2R5D |
|  | PPP2R5E |
|  | PPP3CA |
|  | PPP3CB |
|  | PPP3R1 |

Methods for Isolating Genes Involved in Neurodegeneration
a) C. elegans Screens

Additional genes involved in neurodegeneration may be isolated using the methods described herein. For example, a gene involved in neurodegeneration may be isolated by inducing paralysis and neurodegeneration in C. elegans. This is accomplished, for example, by generating a nematode strain carrying a constitutively active (GTP-ase defective) $G\alpha_s$ subunit gene operably linked to a glutamate receptor (GluR) promoter, such as glr-1. The transgenic C. elegans is screened for gene mutations which restore locomotion and reduce neurodegeneracy (cytotoxicity genes) or which reduce $G\alpha_s$-induced neuronal cell swelling (swelling genes).

I. $G\alpha_s$-associated Cytotoxicity Genes

To isolate a $G\alpha_s$-associated cytotoxicity gene, glr-1::$\alpha_s$ (gf) transgenic nematodes are mutagenized, for example, with EMS or γ-irradiation, and then screened for mutants with both improved locomotion and increased survival of the $G\alpha_s$ expressing neurons. If desired, these mutants may be genetically mapped and placed into complementation groups. The genes identified in these mutants may then be positionally cloned.

II. $G\alpha_s$-associated Swelling Genes

To isolate a $G\alpha_s$-associated swelling gene, glr-1::$\alpha_s$(gf) transgenic nematodes are mutagenized, for example, with EMS or γ-irradiation. First stage larvae are then isolated and screened by fluorescence microscopy (as described herein) for mutants which show a reduced incidence of swelling of $G\alpha_s$-expressing neurons. These mutants may be genetically mapped and positionally cloned.

III. Other Genes

The transgenic animals developed to identify compounds that inhibit cAMP-based neurodegeneration may also be used to identify additional genes involved in neurodegeneration. For example, *C. elegans* doubly transgenic for acy-1::gfp; glr-1::αs(gf) may be mutagenized (for example, with EMS or γ-irradiation) and then analyzed for restored locomotion and reduced neurodegeneration (i.e., for a mutation in a gene which affects the glr-1 promoter) or a reduced level of GFP expression (i.e., for a mutation in a gene which affects the acy-1 promoter), or both (i.e., a mutation in a gene which affects both acy-1 and glr-1 gene promoters).

In an alternative approach, physiological stresses, such as ischemia, due to, for example, the interruption of available oxygen, may be administered to EMS or γ-irradiated worms to induce neurodegeneration. Mutants which resist ischemia-induced neurodegeneration may then be isolated and characterized to identify the neuroprotective mutant gene.

A gene involved in neurodegeneration may be cloned and sequenced by standard methods (see, for example, Ausubel et al., *Current Protocols in Molecular Biology*, John Wiley & Sons, New York, 1994 and Sambrook, Fritsch and Maniatis, *Molecular Cloning: A Laboratory Manual* (2d ed.), CSH Press, 1989). If desired, a protein product from this gene may then be produced, for example, by inserting the cloned gene into an expression vector and introducing this vector into bacterial or eukaryotic cells to produce recombinant proteins. Techniques for such manipulations are disclosed in Sambrook et al., supra, and are well known in the art. Genes involved in neurodegeneration or their protein products may be used in any of the screening or diagnostic assays described herein.

b) Yeast Screens

Another approach to identify genes involved in neurodegeneration utilizes yeast carrying a reporter gene operably linked to a promoter from a cAMP regulatory gene, and, preferably, a mammalian cAMP regulatory gene. The reporter construct is stably introduced into yeast by any standard method. A cDNA library (preferably, from a mammalian cell) is then introduced into the yeast carrying the reporter construct, and yeast colonies exhibiting an increased level of reporter gene expression (e.g., lacZ reporter yeast with increased blue colony color on X-Gal) are identified. Such yeast carry a cDNA capable of binding to the cAMP promoter and are therefor good candidates for a gene involved in cAMP-based neurodegeneration. If desired, the promoter sequences from the newly isolated gene may also be used to generate reporter cells (e.g., reporter yeast or transgenic *C. elegans*) to identify additional genes involved in cAMP-based neurodegeneration.

Moreover, this yeast system may be used to screen for compounds which inhibit the ability of the cDNA to induce reporter gene expression. Such compounds provide good candidates for therapeutics for treating cAMP-based neurodegeneration.

Mammalian Genes Involved in Neurodegeneration a) Mammalian eat-4 genes

Any of a variety of procedures well known in the art may be utilized to clone the mammalian homologues of the nematode eat-4 gene, and one so skilled will routinely adapt one of these methods in order to obtain the desired gene.

One such method for obtaining a mammalian gene sequence is to use an oligonucleotide probe generated by the *C. elegans* eat-4 gene sequence to screen a mammalian cDNA or genomic DNA library for sequences which hybridize to the probe. Hybridization techniques are well known to the skilled artisan, and are described, for example, in Ausubel et al., supra, and Sambrook et al., supra. cDNA or genomic DNA library preparation is also well known in the art. A large number of prepared nucleic acid libraries are also commercially available. The oligonucleotide probes are readily designed using the sequences described herein and standard techniques. The oligonucleotide probes may be based upon the sequence of either strand of DNA encoding the eat-4 gene product (SEQ ID NO: 1). Exemplary oligonucleotide probes are degenerate probes (i.e., a mixture of all possible coding sequences for the EAT-4 protein).

If desired, the cloned gene may be inserted into an expression vector and introduced into bacterial or eukaryotic cells to produce the mammalian EAT-4 protein. Techniques for such manipulations are disclosed, for example, in Sambrook et al., supra. The mammalian eat-4 gene or gene product may be used in the neurodegeneration screening or diagnostic assays described herein.

b) eat-4 related *C. elegans* genes

Genes related to eat-4 may be isolated by methods similar to those described above. For example, a cosmid library from *C. elegans* may be screened with the degenerate oligonucleotide probes described above under low stringency hybridization conditions to isolate eat-4 related *C. elegans* genes. Oligonucleotide probes may be prepared from these gene sequences and may be used to screen mammalian nucleic acid libraries for hybridizing sequences, thus, identifying mammalian homologues of these eat-4 related genes.

All publications and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure come within known or customary practice within the art to which the invention pertains and may be applied to the essential features hereinbefore set forth, and follows in the scope of the appended claims.

Other embodiments are within the claims.

What is claimed is:

1. A method for identifying a gene involved in neurodegeneration, said method comprising the steps of:
   a) providing a nematode comprising an expression construct, said expression construct comprising a promoter derived from a cAMP regulatory gene selected from the group consisting of an acy-1 gene, an eat-4 gene, an unc-36 gene, and a glutamate receptor-encoding gene, said promoter operably linked to a reporter gene;
   b) isolating a nematode comprising a mutation on the basis that said nematode exhibits an altered level of reporter gene expression relative to an unmutated nematode comprising said expression construct; and
   c) identifying said gene comprising said mutation, said gene being involved in neurodegeneration.

2. A method for identifying a gene involved in neurodegeneration, said method comprising the steps of:

a) providing a nematode comprising a glutamate receptor (GluR) promoter operably linked to a gene encoding a GTP-ase defective $G\alpha_s$ subunit;

b) isolating a mutant of said nematode exhibiting a decreased level of paralysis and neurodegeneration; and c) identifying said gene comprising said mutation, said gene being involved in neurodegeneration.

3. The method of claim 1 or 2, wherein said nematode is *C. elegans*.

4. The method of claim 1, wherein said cAMP regulatory gene is an acy-1 gene.

5. The method of claim 1, wherein said cAMP regulatory gene is an eat-4 gene.

6. The method of claim 1, wherein said cAMP regulatory gene is an unc-36 gene.

7. The method of claim 1, wherein said cAMP regulatory gene is a glutamate receptor-encoding gene.

8. The method of claim 1, wherein said reporter gene is selected from the group consisting of lacZ, gfp, her-1, and mec-4.

9. The method of claim 7, wherein said glutamate receptor is selected from the group consisting of GLR-1, C06A8.8, B0280.12, F41B4.4, C43H6, K10D3.1, ZC196.C, GluCLα1, GluCLβ1, ZC317.3, T1063, MGR-1, and F45H11.

10. A method for identifying a gene involved in neurodegeneration, said method comprising the steps of:

a) providing a nematode comprising an expression construct, said expression construct comprising a promoter derived from a cAMP regulatory gene whose product regulates cAMP, said promoter operably linked to a reporter gene;

b) isolating a nematode comprising a mutation on the basis that said nematode exhibits an altered level of reporter gene expression relative to an unmutated nematode comprising said expression construct; and c) identifying said gene comprising said mutation, said gene being involved in neurodegeneration.

11. The method of claim 10, wherein said nematode is *C. elegans*.

12. The method of claim 10, wherein said reporter gene is selected from the group consisting of lacZ, gfp, her-1, and mec-4.

13. The method of claim 10, wherein said cAMP regulatory gene encodes an adenylyl cyclase.

14. The method of claim 10, wherein said cAMP regulatory gene encodes a G protein alpha subunit.

15. The method of claim 10, wherein said cAMP regulatory gene encodes a phosphodiesterase.

16. The method of claim 10, wherein said cAMP regulatory gene encodes a protein phosphatase.

* * * * *